(12) United States Patent
Xiong et al.

(10) Patent No.: US 9,683,991 B2
(45) Date of Patent: Jun. 20, 2017

(54) METHOD OF GENERATING A METAMATERIAL, AND A METAMATERIAL GENERATED THEREOF

(75) Inventors: Qihua Xiong, Singapore (SG); Xinlong Xu, Singapore (SG); Jun Zhang, Singapore (SG)

(73) Assignee: Nanyang Technological University, Singapore (SG)

( * ) Notice: Subject to any disclaimer, the term of this patent is extended or adjusted under 35 U.S.C. 154(b) by 235 days.

(21) Appl. No.: 14/124,496

(22) PCT Filed: Jun. 6, 2012

(86) PCT No.: PCT/SG2012/000203
§ 371 (c)(1),
(2), (4) Date: Mar. 14, 2014

(87) PCT Pub. No.: WO2012/169971
PCT Pub. Date: Dec. 13, 2012

(65) Prior Publication Data
US 2014/0193301 A1    Jul. 10, 2014

Related U.S. Application Data

(60) Provisional application No. 61/494,099, filed on Jun. 7, 2011.

(51) Int. Cl.
*G01N 21/75* (2006.01)
*G01N 33/53* (2006.01)
(Continued)

(52) U.S. Cl.
CPC ............ *G01N 33/5308* (2013.01); *G01J 3/44* (2013.01); *G01N 21/554* (2013.01);
(Continued)

(58) Field of Classification Search
CPC ............ G01N 33/5308; G01N 21/554; G01N 21/658; G01J 3/44; G02B 1/002; G03F 7/2037; G02F 2202/30; G02F 2203/10
See application file for complete search history.

(56) References Cited

U.S. PATENT DOCUMENTS

2008/0160287 A1    7/2008 Misawa et al.
2010/0141358 A1*   6/2010 Akyurtlu ................. H01P 1/20
                                                    333/219.1

OTHER PUBLICATIONS

Clark et al, "Plasmonic Split-Ring Resonators as Dichroic Nanophotonic DNA Biosensors" J. Am. Chem. Soc. Nov. 13, 2009, 131, 17615-17619.*

(Continued)

*Primary Examiner* — Dennis M White
(74) *Attorney, Agent, or Firm* — Alston & Bird LLP

(57) ABSTRACT

A method of generating a metamater-operable in the visible-infrared range is provided. The method comprises a) depositing a layer of a conductive material on a substrate; b) forming a layer of electron beam resist on the layer of conductive material; c) patterning the layer of electron beam resist using electron beam lithography to form a patterned substrate; d) depositing a layer of a noble metal on the patterned substrate; and e) removing the resist. A metamaterial operable in the visible-infrared range comprising split-ring resonators having a least line width of about 20 nm to about 40 nm on a substrate is provided. A transparent photonic device or a sensor for chemical or biological sensing comprising the metamaterial is also provided.

20 Claims, 11 Drawing Sheets

(51) Int. Cl.
- G01J 3/44 (2006.01)
- G01N 21/552 (2014.01)
- G01N 21/65 (2006.01)
- G03F 7/20 (2006.01)
- G02B 1/00 (2006.01)

(52) U.S. Cl.
CPC ........... *G01N 21/658* (2013.01); *G02B 1/002* (2013.01); *G03F 7/2037* (2013.01); *G02F 2202/30* (2013.01); *G02F 2203/10* (2013.01)

(56) References Cited

OTHER PUBLICATIONS

Rockstuhl et al,"Resonances of split-ring resonator metamaterials in the near infrared" Appl. Phys. B 84, 219-227 (2006).*

Ahn, S.H., et al., "Large-Area Roll-to-Roll and Roll-to-Plate Nanoimprint Lithography: A Step toward High-Throughput Application of Continuous Nanoimprinting;" ACS Nano, 2009.3(8): p. 2304-2310.

Alvarez-Puebla, R.A., et al., "Surface-enhanced Raman scattering for ultrasensitive chemical analysis of 1 and 2-naphthalenethiols;"Analyst, 2004. 129: p. 1251-1256.

Anker, J.N., et al., "Biosensing with plasmonic nanosensors;" Nature materials, 2008. 7(6): p. 442-453.

Blaber, M.G., M.D., et al., "Search for the Ideal Plasmonic Nanoshell: The Effects of Surface Scattering and Alternatives to Gold and Silver;" The Journal of Physical Chemistry C, 2009. 113: p. 3041-3045.

Chen, H., et al., "Plasmon-molecule interactions;" Nano Today, 2010. 5: p. 494-505.

De Hoogh. A. et al., "Wavelength-selective addressing of visible and near-infrared plasmon resonances for SU8 nanolithography;" Optics Express, 2011, vol. 19, No. 12, pp. 11405-11414.

Di Falco, A. et al., "Flexible metamaterials at visible wavelengths;" New Journal of Physics, 2010, vol. 12, 113006, pp. 1-7.

Driscoll, T., et al., "Tuned permeability in terahertz split-ring resonators for devices and sensors;" Applied Physics Letters, 2007. 91(6): p. 062511

Enkrich, C., et al., "Magnetic metamaterials at telecommunication and visible frequencies;" Physical Review Letters, 2005. 95.

Fedotov, V.A., et al., "Sharp Trapped-Mode Resonances in Planar Metamaterials with a Broken Structural Symmetry;" Physical Review Letters, 2007. 99(14): p. 147401.

Gu, Y. et al., "Plasmonic metamaterials for ultrasensitive refractive index sensing at near infrared;" Journal of Applied Physics, 2011. 109(2): p. 023104.

Jain, P.K., et al., "On the universal scaling behavior of the distance decay of plasmon coupling in metal nanoparticle pairs: a plasmon ruler equation;" Nano Letters, 2007. 7(7): p. 2080-2088.

Jeppesen, C., et al., "Metamaterial localized resonance sensors: prospects and limitations;" Opt. Express, 2010. 18(24): p. 25075-25080.

Jeppesen, C. et al., "The effect of Ti and ITO adhesion layers on gold split-ring resonators;" Applied Physics Letters, 2010, vol. 97, pp. 263103-(1-3).

Kabashin, A.V., et al., "Plasmonic nanorod metamaterials for biosensing;" Nature materials, 2009.

Kolega, R.R. et al., "Self-assembled monolayers of an aryl thiol: Formation, stability, and exchange of adsorbed 2-naphthalenethiol and his (2-naphthyl) disulfide on Au;" Langmuir, 1998. 14(19): p. 5469-5478.

Lal, S., et al., "Nano-optics from sensing to waveguiding;" Nature Photonics, 2007. 1(11): p. 641-648.

Leung, K.L. et al., "Characterization of microfibrillar reinforced poly(ethylene naphthalate)/polypropylene composites via polarized Raman and polarized FTIR spectroscopy;" Journal of Applied Polymer Science, 2010. 116: p. 1442-1449.

Liedberg, B., et al., "Biosensing with surface plasmon resonance—how it all started;" Biosensors and Bioelectronics, 1995. 10.

Liedberg, B., et al., "Surface plasmon resonance for gas detection and biosensing;" Sensors and Actuators, 1983. 4: p. 299-304.

Linden, S., et al., "Magnetic response of metamaterials at 100 terahertz;" Science, 2004. 306: p. 1351-1353 and supporting online materials.

Liu, N. et al., "Coupling Effects in Optical Metamaterials;" Angewandte Chemie International Edition, 2010. 49: p. 9838-9852.

Liu, N., et al., "Infrared Perfect Absorber and Its Application As Plasmonic Sensor;" Nano Letters, 2010. 10: p. 2342-2348.

Liu, N., et al., "Planar metamaterial analogue of electromagnetically induced transparency for plasmonic sensing;" Nano Letters, 2010. 10: p. 1103-1107.

Liu, N., et al., "Three-dimensional photonic metamaterials at optical frequencies;" Nature materials, 2007. 7(1): p. 31-37.

Marqués, R., et al., "Role of bianisotropy in negative permeability and left-handed metamaterials;" Physical Review B, 2002. 65(14): p. 144440.

Melik, R., et al., "Flexible metamaterials for wireless strain sensing;" Applied Physics Letters, 2009. 95: p. 181105.

Melik, R., et al., "Metamaterial based telemetric strain sensing in different materials;" Opt. Express, 2010. 18(5): p. 5000-5007.

Oskooi, A.F., et al., "MEEP: A flexible free-software package for electromagnetic simulations by the FDTD method;" Computer Physics Communications, 2010. 181(3): p. 687-702.

Papasimakis, N., et al., "Graphene in a photonic metamaterial;" Opt. Express, 2010. 18(8): p. 8353-8359.

Pendry, J., et al., "Magnetism from conductors and enhanced nonlinear phenomena;" IEEE Transactions on Microwave Theory and Techniques, 1999. 47(11): p. 2075-2084.

Pryce, I.M., et al., "Highly Strained Compliant Optical Metamaterials with Large Frequency Tunability;" Nano Letters, 2010. 10(10): p. 4222-4227.

Rockstuhl, C., et al., "On the reinterpretation of resonances in split-ring-resonators at normal incidence;" Opt. Express, 2006. 14(19): p. 8827-8836.

Shalaev, V.M., et al., "Negative index of refraction in optical metamaterials;" Optics Letters, 2005. 30(24): p. 3356.

Shelby, R., et al., "Experimental verification of a negative index of refraction;" Science, 2001. 292: p. 77-79.

Shelton, D.J., et al., "Effect of thin silicon dioxide layers on resonant frequency in infrared metamaterials;" Opt. Express, 2010. 18(2): p. 1085-1090.

Smith, D.R., et al., "Metamaterials and negative refractive index;" Science, 2004. 305: p. 788-792.

Sonnichsen, C., et al., "A molecular ruler based on plasmon coupling of single gold and silver nanoparticles;" Lawrene Berkeley National Library, 2005, p. 1-13.

Tao. H. et al., "Performance enhancement of terahertz metamaterials on ultrathin substrates for sensing applications;" Applied Physics Letters, 2010, vol. 97. pp. 261909-(1-3).

Tao, H., et al., "Terahertz metamaterials on free-standing highly-flexible polyimide substrates;" Journal of Physics D: Applied Physics, 2008. 41: p. 232004.

Theiss, J., et al., "Plasmonic Nanoparticle Arrays with Nanometer Separation for High-Performance SERS Substrates;" Nano Letters, 2010. 10: p. 2749-2754.

Ulman, A., "Formation and Structure of Self-Assembled Monolayers;" Chemical Reviews, 1996. 96(4): p. 1533-1554.

Xu, X., et al., "Bianisotropic response of microfabricated metamaterials in the terahertz region;" Journal of the Optical Society of America-B-Optical Physics, 2006. 23(6): p. 1174-1180.

Yanik, A.A., et al., "An Optofluidic Nanoplasmonic Biosensor for Direct Detection of Live Viruses from Biological Media;" Nano Letters, 2010. 10: p. 4962-4969.

Yen, T.J., et al., "Terahertz magnetic response from artificial materials;" Science, 2004. 303: p. 1494-1496.

Zayak, A.T., et al., "Chemical Raman Enhancement of Organic Adsorbates on Metal Surfaces;" Physical Review Letters, 2011. 106(8): p. 083003.

Zheludev, N.I., "The road ahead for metamaterials;" Science, 2010.328: p. 582-583.

(56) References Cited

OTHER PUBLICATIONS

Zheng, G., et al., "*Frequency Domain Detection of Biomolecules Using Silicon Nanowire Biosensors*;" Nano Letters, 2010. 10: p. 3179-3183.
Zheng, G., et al., "*Multiplexed electrical detection of cancer markers with nanowire sensor arrays*;" Nature Biotechnology, 2005. 23(10): p. 1294-1301.
International Preliminary Report on Patentability for Application No. PCT/SG2012/000203; dated Jun. 19, 2013.
International Search Report and Written Opinion for Application No. PCT/SG2012/000203; dated Oct. 5, 2012.
"*NANO™ PMMA and Copolymer*;" Micro.Chem, dated 2001; retrieved from <www.microchem.com/products/pdf/PMMA_Data_Sheet.pdf>.

* cited by examiner (A)

(B)

(i)     (ii)     (iii)     (iv)     (v)     (vi)

(C)

(i)     (ii)     (iii)     (iv)     (v)     (vi)

(D)

(A)

(B)

(C)

METHOD OF GENERATING A METAMATERIAL, AND A METAMATERIAL GENERATED THEREOF

CROSS-REFERENCE TO RELATED APPLICATIONS

This application makes reference to and claims the benefit of priority of an application for "Flexible Vis-IR Metamaterials and Their Applications in Highly Sensitive Chemical and Biological Sensing" filed on Jun. 7, 2011, with the United States Patent and Trademark Office, and there duly assigned Ser. No. 61/494,099. The content of said application filed on Jun. 7, 2011, is incorporated herein by reference in its entirety for all purposes.

TECHNICAL FIELD

The invention relates to a method of generating a metamaterial and a metamaterial generated thereof.

BACKGROUND

Metamaterials have been shown as an effective way to enhance the engineering and manipulating of plasmon and photon in the area of optics. By using "artificial atoms" such as split ring resonators (SRRs) within a metamaterial, metamaterials with optical properties beyond the limitations of conventional, naturally occurring material or composites may be obtained. Realization of electromagnetic response for metamaterials in the visible and infrared (vis-IR) regions may open up a whole new range of photonic application areas, such as security imaging, remote sensing, and switchable and transformable optical frequency resonant devices.

Provision of flexibility to metamaterials in various applications, in particular, sensing is also of interest. Integration of functional, high-performance electronic devices onto mechanically flexible and deformable substrates offers significant promise in flexible electronics, such as flexible displays, solar cells, nanowire electronics, and sensing circuitry. Compared to rigid substrates such as silicon and glass, flexible and stretchable plastic or elastomer based substrates exhibit great advantages of flexibility, transparency, lightweight, portability, low cost, conformable manipulation, and biocompatibility. On the other hand, recent development of transformation optics based on topological design and manipulation of light renders flexible functional optics an attractive option to control optical waves, which may in turn lead to integration of functional flexible photonic devices as demonstrated in strained tunability applications. In other application areas, for example, flexibility in metamaterials may make it possible to "wrap" light-weight, transparent metamaterials around important objects to function as an optical cloak. Current state of the art methods to fabricate metamaterials, in particular metamaterials based on flexible materials, include use of an indirect transfer method to embed metamaterials into flexible elastomeric matrix after the metamaterials have been fabricated onto rigid and flat substrates, such as silicon and quartz. However, these methods suffer from drawbacks, such as limitations relating to resolution of metamaterials obtained, and the lengthy process sequences required. This is particularly the case for applications in the visible and infrared range, given the extremely high resolution of metamaterials required.

In view of the above, there is a need for an improved method to generate a metamaterial and a metamaterial generated thereof that alleviates at least some of the above-mentioned problems.

SUMMARY OF THE INVENTION

In a first aspect, the invention refers to a method of generating a metamaterial operable in the visible-infrared range. The method comprising
 a) depositing a layer of a conductive material on a substrate;
 b) forming a layer of electron beam resist on the layer of conductive material;
 c) patterning the layer of electron beam resist using electron beam lithography to form a patterned substrate;
 d) depositing a layer of a noble metal on the patterned substrate; and
 e) removing the resist.

In a second aspect, the invention refers to a metamaterial generated by a method according to the first aspect.

In a third aspect, the invention refers to a metamaterial operable in the visible-infrared range comprising split-ring resonators having a least line width of about 20 nm to about 40 nm on a substrate.

In a fourth aspect, the invention refers to a transparent photonic device or a sensor for chemical or biological sensing comprising a metamaterial according to the second aspect or the third aspect.

In a fifth aspect, the invention refers to use of a metamaterial according to the second aspect or the third aspect in optical filter, magneto filter, polarization detector, photonic device and sensor.

BRIEF DESCRIPTION OF THE DRAWINGS

The invention will be better understood with reference to the detailed description when considered in conjunction with the non-limiting examples and the accompanying drawings, in which:

FIG. 7D is a schematic diagram of SRRs with $L_x=200$ nm, $L_y=200$ nm, $S_x=S_y=200$ nm, w=50 nm, a=100 nm, and $d_x=d_y=100$ nm for V-shape. The whole unit size and the periodicity of the unit cell were decreased accordingly in order to push to visible regime. The actual width w values have been specified in the boxes on the right of each figure.

FIGS. 8(E), (F), (G) and (H) correspond respectively to the SEM picture of metamaterials with w=50 nm for the different geometry shapes with Raman spectra shown in FIGS. 8(A), (B), (C) and (D). The scale bar in FIGS. 8(E), (F), (G) and (H) denote a length of 100 nm.

DETAILED DESCRIPTION OF THE INVENTION

Figure 1:
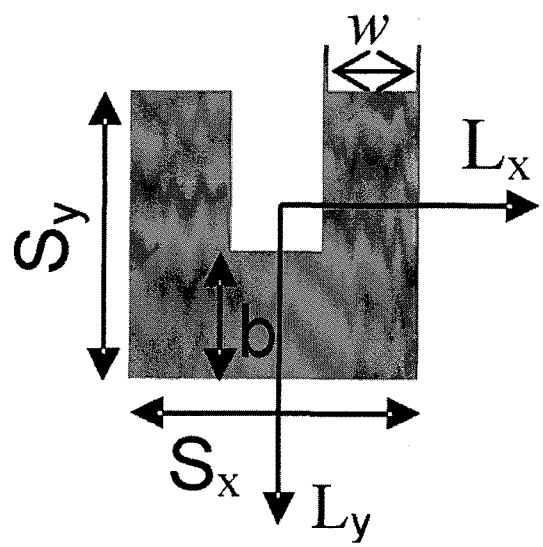
FIG. 1A is a schematic diagram of a U-shaped split-ring resonator (SRR) with $L_x$ denoting periodicity in the x-direction; $L_y$ denoting periodicity in the y-direction; $S_x$ and $S_y$ denoting edge dimensions of split-ring resonator in the x-direction and y-direction respectively; b denoting thickness of the bottom region of the letter "U" as indicated in the figure; w denoting the least line width of the U-shaped SRR. In an illustrated embodiment, $L_x$=504 nm, $L_y$=480 nm, $S_x$=$S_y$=320 nm, w=80 nm, and b=128 nm.
FIG. 1B is a schematic diagram showing a decrease of the whole unit size and periodicity of the unit cell for operation in the visible regime, where w equals (i) 80 nm, (ii) 70 nm, (iii) 60 nm, (iv) 50 nm, (v) 40 nm, (vi) 30 nm.
FIG. 1C is a series of scanning electrode microscopy (SEM) images of the unit cells of the SRRs, where w equals (i) 80 nm, (ii) 70 nm, (iii) 60 nm, (iv) 50 nm, (v) 40 nm, (vi) 30 nm (scale bar in the images depicts 100 nm).
FIG. 1D depicts a typical scanning electron microscopy (SEM) image (45° tilted) of SRRs with w=80 nm fabricated on a poly(ethylene naphthalate) (PEN) substrate.
Figure 1:
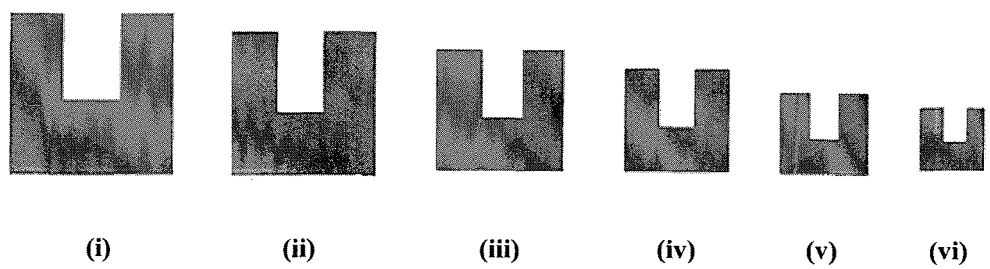
Figure 1:
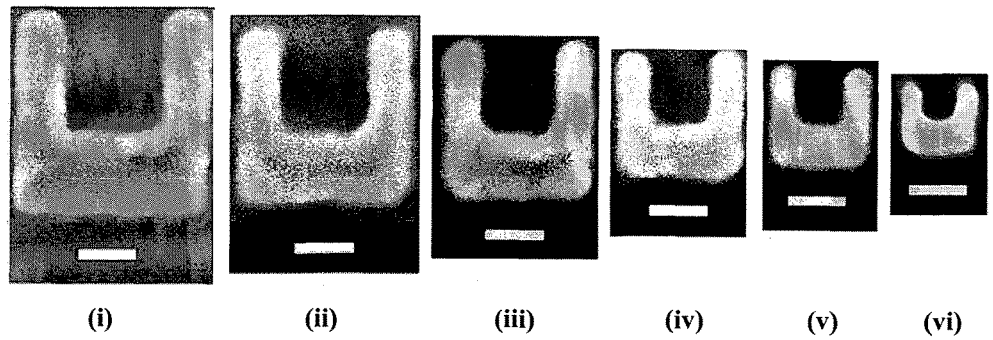
Figure 1:
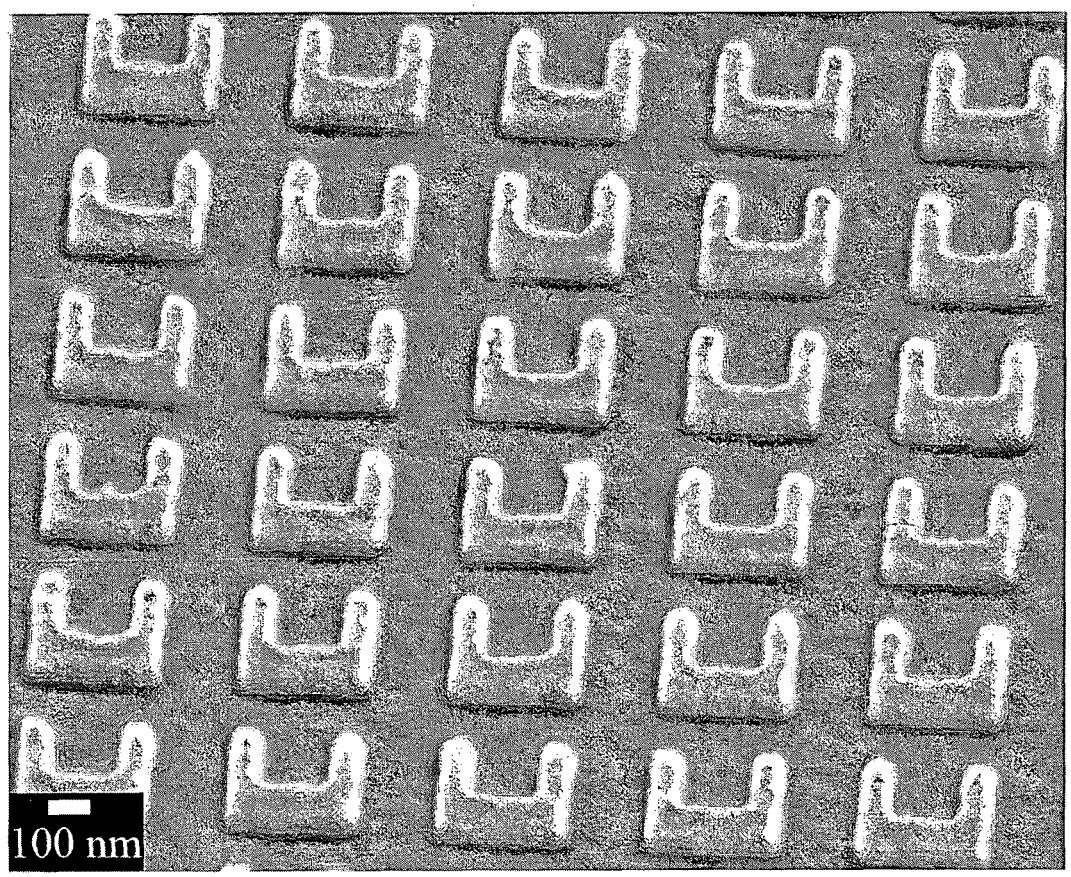

In a first aspect the present invention refers to a method of generating a metamaterial operable in the visible-infrared range.

As used herein, the term "metamaterial" refers generally to an artificial material that is engineered to exhibit and/or to provide electromagnetic behavior that is not found in a natural material. For example, metamaterials may be designed to provide electric or magnetic resonances where there are no equivalent materials in nature. This may be carried out by patterning one or more elements that are comprised in a metamaterial in one or more dimensions, with each element having physical dimensions less than or on the order of an incident wavelength in the direction of wave propagation. In so doing, each of the elements comprised in the metamaterial may be patterned to exhibit specific electric and magnetic polarizations in response to an applied electromagnetic field.

For example, a metamaterial may be configured to simultaneously possess negative permeability and negative permittivity, such that electromagnetic waves passing through this medium exhibit certain "unnatural" characteristics. One of these unnatural characteristics may be in the form of a reversal in the right-handed rule, in which electric and magnetic fields follow with regards to the propagation vector of the wave. In these metamaterials, a left-handed relationship may exist between these vector quantities. Accordingly, such metamaterials may be termed as "left-handed materials (LHM)". In another example, a metamaterial may be configured to exhibit a negative refractive index. Accordingly, such metamaterials may be termed as "negative index materials (NIM)". Equipped with such attributes, these metamaterials are useful in elecromagnetics, where they may be used in fabricating novel antennas, filters and waveguides for electromagnetic communications.

Examples of metamaterial include, but are not limited to, lattices formed from straight wire conductors and arrays of split-ring resonators, both of which may be fabricated on a suitable substrate. The terms "element", "unit cell", and "resonator" are used interchangeably herein, and refer to a structure having, or capable of having, a desired mechanical or electro-mechanical vibration.

The method of generating a metamaterial operable in the visible-infrared region may be carried out on rigid substrates such as silicon or quartz, and on flexible substrates such as a polymer. The method of the invention may be used to generate metamaterials having dimensions which are sufficiently small for use in the visible-infrared range. In particular, it has been demonstrated herein that an electron-beam lithography (EBL) nanofabrication method may be used to generate flexible metamaterials operable in the visible-infrared region.

The method of the invention includes depositing a layer of a conductive material on a substrate. The conductive material may be electrically conductive. In various embodiments, the conductive material comprises a transparent material, such as a material having high transparency in the visible and/or infrared wavelength range. As used herein, the visible range of the electromagnetic spectrum refers generally to electromagnetic waves having a wavelength in the range of about 380 nm to about 780 nm. The infrared range of the electromagnetic spectrum, on the other hand, refers to electromagnetic waves having a wavelength that is greater than 780 nm.

Examples of conductive materials that may be used in the method of the invention include, but are not limited to, indium tin oxide, indium zinc oxide, tin oxide and alloys thereof. In various embodiments, the conductive material comprises indium tin oxide. In some embodiments, the conductive material consists of indium tin oxide.

The conductive material may be deposited by any suitable thin film coating method. Examples of coating methods that may be used include sputtering, vapor deposition and electron beam deposition. In one embodiment, sputtering is used. Generally, the conductive material may be of any thickness, so long as it is able to alleviate or eliminate the charging effect as a result of action of electron beam on the substrate. Accordingly, in various embodiments, the conductive material referred to herein is an electrically conductive material. The layer of conductive material may be sufficiently thin so as not to affect the transparency of the resulting metamaterial. In embodiments where indium tin oxide is used as the conductive material, for example, the thickness of the indium tin oxide layer may be about 50 nm to about 200 nm, such as about 50 nm to about 150 nm, about 50 nm to about 100 nm, or about 100 nm to about 200 nm. In one embodiment, the thickness of the indium tin oxide layer is about 100 nm.

The method of the invention includes forming a layer of electron beam resist on the layer of conductive material. The electron beam resist may comprise at least one of poly (methyl methacrylate) and polymethylglutarimide. In various embodiments, the electron beam resist comprises substantially of poly(methyl methacrylate). The electron beam resist may be formed by any suitable coating method such as, but not limited to, spin-coating, painting, dip-coating, spray coating, and screen painting. In various embodiments, the electron beam resist layer is formed by spin-coating.

The layer of electron beam resist is patterned using electron beam lithography to form a patterned substrate. Electron beam lithography refers to a method of patterning a surface using a beam of electrons. By directing an electron beam onto the layer of electron beam resist, a specific pattern may be written onto the resist layer. In embodiments whereby a polymeric substrate is used, electric charge that may be induced on the substrate as a result of patterning by the electron beam may be alleviated by the layer of conductive material deposited thereon. After a corresponding development step, depending on the type of resist used, either of the exposed or unexposed portions of the resist material may be removed to leave behind the corresponding unexposed or exposed portions of the resist layer.

In various embodiments, the patterned resist defines a template or mold for subsequent formation of an array of elements or resonators of the metamaterials. In some embodiments, the elements or resonators are arranged in an orderly or periodic sequence, such as that shown in FIG. 1D. The patterned resist may cover portions of the substrate upon which the resonators are not formed. In various embodiments, the resonators may be split-ring resonators. In general terms, a split-ring resonator refers to a type of resonator, comprising a conductive ring that is broken in at least one location on the ring by a non-conductive gap of air or other dielectric material. When the split-ring resonator is placed in an electro-magnetic field, fluctuation of the electro-magnetic field causes a circular electric current to be induced in the conductive ring, which in turn results in charge accumulation across the gap(s) in the ring. The electric field that builds due to the charge at the gap counteracts the circular current, leading to storage of substantial amounts of energy in the vicinity of the gaps. In addition, magnetic field energy is concentrated in the region enclosed by the ring. Accordingly, a split ring resonator may be considered as a resonator that reacts to a perpendicular magnetic field, and may be characterized by the effective capacitance of the gaps and effective inductance of the loop defined by the ring.

To form the resonators on the substrate, a layer of a noble metal is deposited on the patterned substrate. The noble metal may be deposited by any suitable methods, such as thermal evaporation or electron beam evaporation. Some of the noble metal deposited may be present on the patterned resist, while some portions of the noble metal layer may be present on the substrate that is not covered by the resist. By removing the patterned resist layer in a subsequent step, the noble metal that is coated on the patterned resist is removed as well, leaving behind the noble metal layer present on portions of the substrate, which are not covered by the resist, to form the resonators. Examples of a noble metal include silver (Ag), palladium (Pd), gold (Au), platinum (Pt), iridium (Ir), osmium (Os), rhodium (Rh) and ruthenium (Ru). In various embodiments, the noble metal comprises gold, silver, or alloys thereof. In one embodiment, the noble metal consists substantially of gold. The thickness of the noble metal layer may range from about 5 nm to about 500 nm on the surface of the patterned substrate, such as about 5 nm to about 200 nm, about 5 nm to about 100 nm, about 5 nm to about 50 nm, about 5 nm to about 20 nm, or about 30 nm.

In various embodiments, the method of the invention includes depositing an adhesion layer on the patterned substrate prior to deposition of the noble metal layer. The adhesion layer may be deposited to improve adhesion of the noble metal to the patterned substrate. Examples of material that may be used as the adhesion layer include chromium, titanium, and alloys thereof. In various embodiments, the adhesion layer comprises chromium. In one embodiment, chromium was used as the adhesion layer. The adhesion layer may be deposited using any suitable methods, such as thermal evaporation or electron beam evaporation. In one embodiment, thermal evaporation was used to deposit a layer of chromium on the patterned substrate. The thickness of the layer of chromium may be of any suitable value that is able to improve adhesion of the noble metal to the patterned substrate. In various embodiments, the thickness of the chromium layer is about 1 nm to about 10 nm, such as about 5 nm to about 10 nm or about 1 nm to about 5 nm. In one embodiment, 2 nm of chromium was deposited on the patterned substrate.

After the noble metal is deposited on the patterned substrate, the resist may be removed. For example, the resist may be removed using a suitable solvent. Depending on the type of resist used, the resist may additionally or alternatively be removed using plasma. By removing the patterned resist layer, the noble metal layer, that is present on the substrate not covered by the resist and which is left behind on the substrate, form the resonators. Accordingly, in removing the patterned resist from the substrate, a metamaterial operable in the visible-infrared range may be obtained.

In a second aspect, the invention refers to a metamaterial operable in the visible-infrared range generated by a method according to the first aspect. The invention also relates, in a further aspect, to a metamaterial that is operable in the visible-infrared range comprising split-ring resonators having a least line width of about 20 nm to about 40 nm on a substrate.

The split-ring resonators comprised in the metamaterial of the invention have a least line width of about 20 nm to about 40 nm. The term "least line width" refers to the smallest dimension on the periphery of the split-ring resonator. Referring to FIG. 1A, for example, where a U-shaped split-ring resonator is shown, the least line width is denoted by the letter w. In various embodiments, the split-ring resonators have a least line width of about 20 nm to about 25 nm. In one embodiment, the split-ring resonators have a least line width of about 30 nm. Even though FIG. 1A denotes a U-shaped split-ring resonator, other shapes may be used. For example, the split-ring resonator may be formed from the letter "O" and having a gap in the letter. For such a shape, the least line width may correspond to the width of the split-ring resonator at the gap portion.

Generally, split-ring resonators which are composed from a basic shape of "U" or "V" may be used. For example, the split-ring resonator may be formed from a single "U" arranged in any orientation, such as C-shaped, reverse C-shaped (i.e. mirror image of a C-shaped), U-shaped, reverse U-shaped (i.e. mirror image of a U-shaped, or n-shaped), or a U shape oriented at any angle to the vertical axis. As another example, the split-ring resonator may be formed from a single "V" arranged in any orientation, such as V-shaped, reverse V-shaped, >-shaped, <-shaped, or a V shape oriented at any angle to the vertical axis. The split-ring resonator may also be formed from a plurality of "U","V", or their combination. For example, the split-ring resonator may be formed from two "U" and/or two "V" arranged in any orientation, such as E-shaped, H-shaped, I-shaped, M-shaped, S-shaped, W-shaped, Y-shaped, Z-shaped, or their reverse. In various embodiments, the split-ring resonators are C-shaped, E-shaped, H-shaped, S-shaped, U-shaped, U-bar shaped (i.e. "Ū"), V-shaped, W-shaped or Y-shaped. Each of the two "U" and/or "V" may be of the same size or a different size. For example, where two "U" are arranged to form a S-shaped resonator, the top portion of the S-shaped resonator (the first "U") may be smaller than the bottom portion of the S-shaped resonator (the second "U"). Accordingly, the least line width w of each "U" or "V" that is used to form the S-shaped resonator may be the same or different. When they are combined and arranged to form a single shape "S", the least line width of the S-shaped resonator corresponds to the smallest dimension on the periphery of the split-ring resonator, which may be the smaller w of each of the two "U" or "V". As discussed herein, although the split-ring resonators are generally formed from two "U" and/or "two "V", the split-ring resonator may also be formed from three, four or five "U" and/or "V" arranged in any orientation, so long as the least line width of the formed shape is about 20 nm to about 40 nm, thereby rendering it operable in the visible-infrared range.

Figure 7:
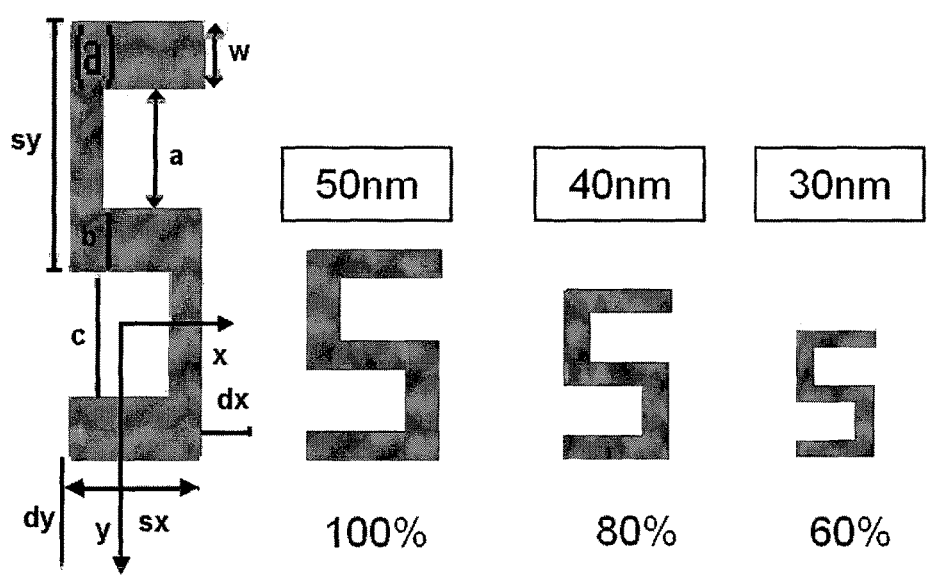
FIG. 7 is a series of schematic diagrams of SRRs with $L_x=200$ nm, $L_y=350$ nm, $S_x=S_y=200$ nm, w=50 nm, a=c=100 nm, b=50 nm and $d_x=d_y=100$ nm for (A) S-shape, (B) H-shape, and (C) Y-shape.
Figure 7:
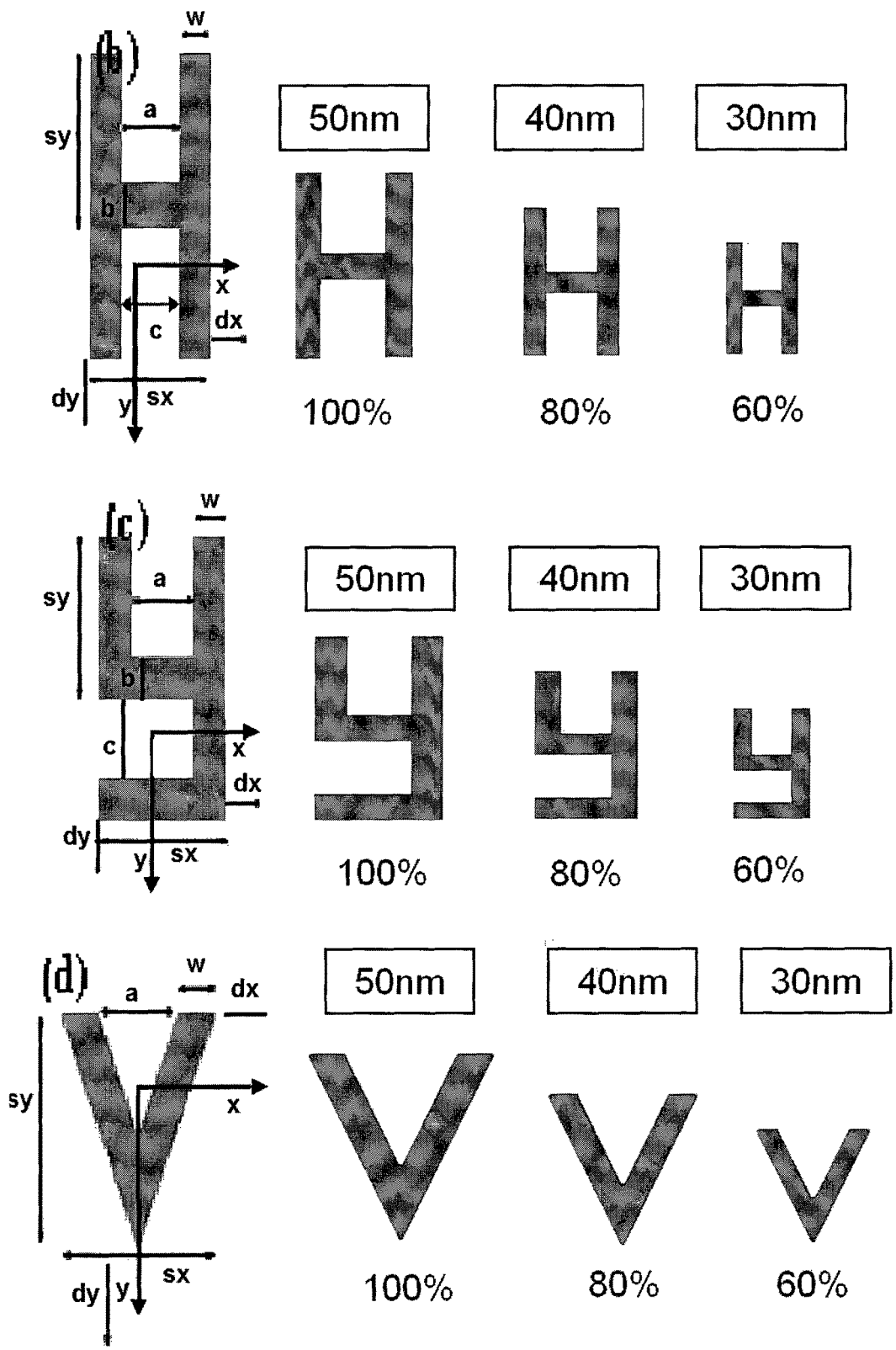
Figure 8:
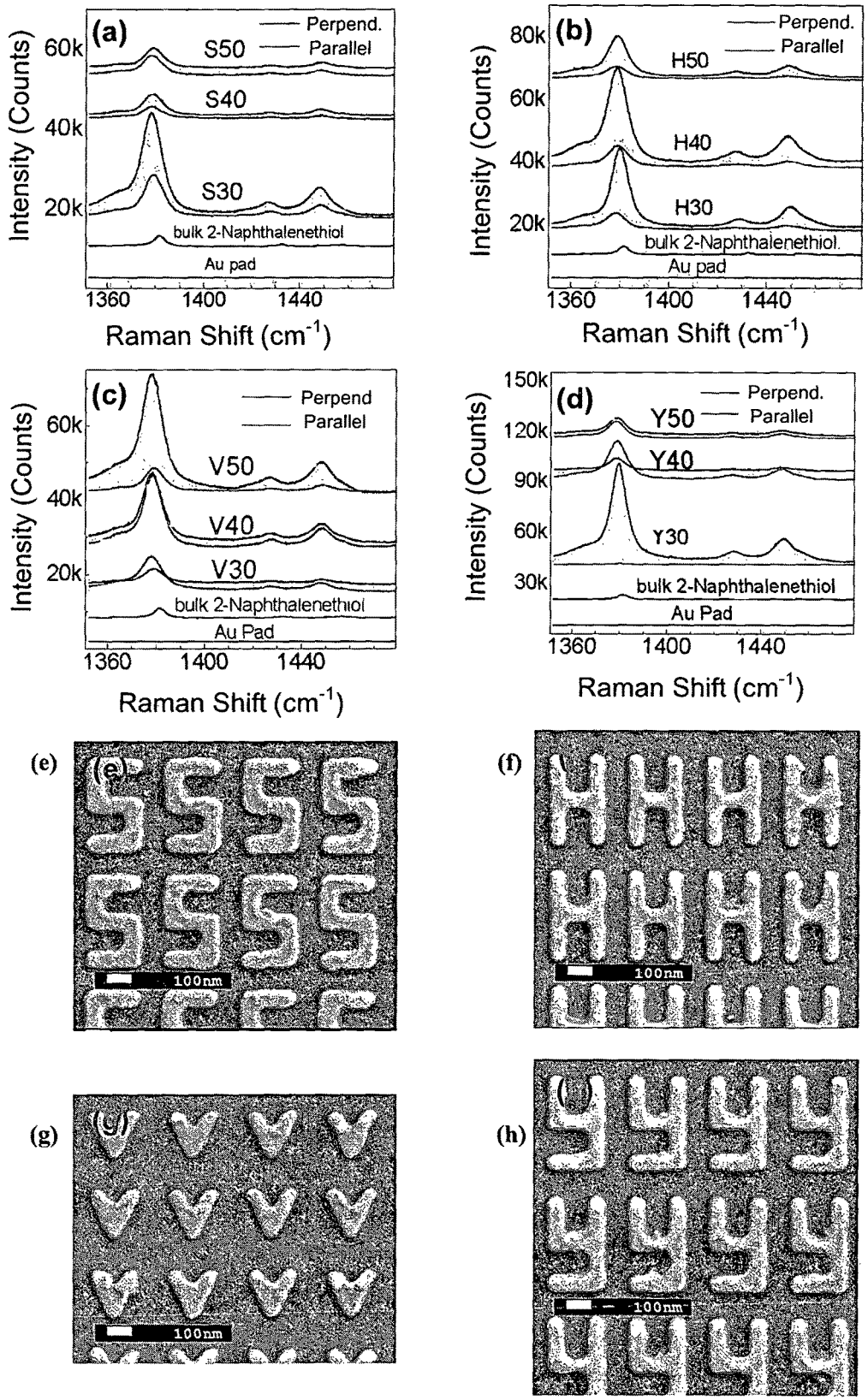
FIG. 8 are graphs showing Raman spectra of 2-naphthalenethiol on metamaterial samples with polarization perpendicular or parallel as shown in (A) S-shape, (B) H-shape, (C) V-shape, and (D) Y-shape. The Raman spectra from 2-Naphthalenethiol powder, and from a gold pad film on the same substrate also are shown.

FIG. 7 shows the corresponding split-ring resonators having the least line width w indicated in the figure. In one embodiment, the split-ring resonators are Y-shaped. The Y-shaped split-ring resonators may have a least line with of about 30 nm. It has been surprisingly found by the inventors of the invention that Y-shaped split-ring resonators, such as that shown in FIG. 7C, with least line width of 30 nm provide the highest enhancement of surface enhanced Raman scattering (SERS) signal compared to the split-ring resonators of the other shapes.

The split-ring resonators may comprise a noble metal, which may be present in the form of a layer of noble metal on the surface of the split-ring resonators. Examples of noble metals have already been described above. In various embodiments, the noble metal is present as a layer having a thickness of about 5 nm to about 500 nm on the surface of the split-ring resonators. In one embodiment, the thickness of the layer of noble metal is about 30 nm.

A layer of conductive material may be present between the layer of noble metal and the substrate. In various embodiments, the conductive material may be a transparent material, for example, a material that is highly transparent in the visible or infrared range. The conductive material may be an electrically conductive material. By virtue of the layer of conductive material, electron beam lithography may be used to form the split-ring resonators on a non-conductive substrate, for example. Examples of conductive materials that may be used in the method of the invention include, but are not limited to, indium tin oxide, indium zinc oxide, tin oxide and alloys thereof. In various embodiments, the conductive material comprises indium tin oxide. In some embodiments, the conductive material consists of indium tin oxide.

Metamaterials according to various embodiments of the invention may be based on either rigid substrates, such as silicon or glass, or transparent flexible substrate, for example, a polymer such as polyethylene naphthalate (PEN) and polyethylene terephthalate (PET). In some embodiments, the substrate may be a non-electrically conductive material, which may be rigid or flexible. The substrate may comprise a transparent material. In various embodiments, a flexible substrate such as polyethylene naphthalate is used. PEN may be preferred in some applications as it has a higher glass transition temperature compared to other polymers, and is solvent-, acid- and base-resistant. Depending on the type of application, other types of polymer may be used.

The split-ring resonators may be arranged in a periodic array. In various embodiments, the periodicity along the x-axis of the split-ring resonators is in the range of about 50 nm to about 1000 nm. For example, the periodicity along the x-axis of the split-ring resonators may be about 50 nm to about 500 nm, about 50 nm to about 250 nm, or about 50 nm to about 100 nm. In various embodiments, the periodicity along the y-axis of the split-ring resonates is in the range of about 50 nm to about 1000 nm, such as about 50 nm to about 500 nm, about 50 nm to about 250 nm, or about 50 nm to about 100 nm. As mentioned earlier, it has been demonstrated herein that an electron-beam lithography nanofabrication method may be used to generate flexible metamaterials operable in the visible-infrared region. In this regard, the use of a method of the present invention is particularly advantageous in generating metamaterials comprising split-ring resonators with dimensions which are sufficiently small for use in the visible-infrared range.

The metamaterials according to various embodiments of the invention have been demonstrated to possess high sensitivity, high tunability, flexibility, and multiplex sensing application in the visible-infrared region. Depending on the intended application, the metamaterial may be based on a flexible substrate or a rigid substrate. Due to the small feature size of elements or resonators on the metamaterials for operating in the visible-infrared region, the use of electron-beam lithography greatly enhances the resolution and yield of the metamaterial generated. This is particularly in the case for flexible substrates such as polymers, where the application of electron beam processes is not utilized, as a result of detrimental charging effects of the electron beam on the polymeric material. The method of the invention addresses this issue through the deposition of a conductive layer on the polymeric substrate, which alleviates or eliminates the charging effect as a result of bombardment of the electron beam on the substrate. Furthermore, use of the electron beam lithography process allows the size and geometry of the metamaterial structure to be easily customized to suit specific applications, since both the absorption band and the local field enhancement contour can be tuned or controlled simultaneously.

In a fourth aspect, the invention relates to a transparent photonic device, or a sensor for chemical or biological sensing comprising a metamaterial according to the second aspect or the third aspect. The sensor according to various embodiments of the invention may utilize two types of sensing. The first type of sensing is based on the plasmon-related transmission change, which may be sensitive to constant changes in micro-environmental conditions of the dielectric. The second type of sensing is related to surface-enhanced Raman scattering, which may be used for single-molecular finger-printing identification. Combination of the two effects, which have not been achieved in state of the art methods, may be used in the sensor of the present invention.

The sensor may further comprise linker molecules bonded to the surface of the metamaterial. In so doing, the metamaterial may be specifically binded or associated with target analytes via the linker molecules for analysis. In various embodiments, the linker molecules are covalently bonded to the surface of the metamaterial. The linker molecules may comprise a functional group selected from the group consisting of thiol, amine, amide, nitro, carboxylic acid, cyano and halogen. For example, when the metamaterial comprises split-ring resonators having gold deposited on the surface of the split-ring resonators, linker molecules comprising a thiol group may be used.

By detecting peak shifts in the surface enhanced Raman spectrum obtained of a sample to that of a reference spectrum, or by comparisons to a spectrum retrieved under known conditions, for example, the target analytes in the sample may be identified. The term "sample", as used herein, refers to an aliquot of material, an aqueous solution or an aqueous suspension suspected to contain a target analyte. In various embodiments, the sample is derived from biological material. For example, the samples may comprise cells, tissues, homogenates, lysates, extracts, and purified or partially purified proteins and other biological molecules and mixtures thereof. The sample may also be a chemical solution. For example, the samples may comprise chemical species, such as contaminants in ground water, for example, for identification. In various embodiments, the extent of the peak shifts in the surface enhanced Raman spectrum may be correlated with the amount of target analytes in the sample.

In line with the above, the invention relates, in a further aspect, to use of the metamaterial according to the second aspect or the third aspect in optical filter, magneto filter, polarization detector and sensor.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

Split-Ring Resonance Structure Design

The geometrical parameters that describe the U-shape SRRs demonstrated in the experiments are shown in FIG. 1A. FIG. 1A is a schematic diagram of a U-shaped split-ring resonator (SRR), with $L_x$ and $L_y$ denoting periodicities of the unit cell of SRR along the x-direction and y-direction respectively; $S_x$ and $S_y$ denoting edge dimensions of split-ring resonator in the x-direction and y-direction respectively; b denoting thickness of the lower region of the letter "U" as indicated in the figure; and w denoting the least line width of the U-shaped SRR.

In the experiments carried out, the U-shape SRRs has the following dimensions: $L_x$=504 nm, $L_y$=480 nm, $S_x$=$S_y$=320 nm, w=80 nm, and b=128 nm. In order to push the electric response from infrared to visible region, the whole unit size of SRRs including the unit cell was reduced down to 37.5% (100% corresponds to original size as defined in FIG. 1A), which decreases the value of w from 80 nm to 30 nm.

Example 2

Fabricating the Metamaterial

The metamaterial was fabricated using electron beam lithography (EBL) on polyethylene naphthalate (PEN) substrates (Teijin DuPont Films). The PEN substrates were first sputtered on a layer of indium tin oxide (ITO) with a thickness of 100 nm to decrease the charging effect. Commercial electron beam resist poly(methyl methacrylate) (PMMA) (950 A4, Microchem, USA) was spin-coated at 4,000 rpm and baked at 180° C. A JEOL 7001F scanning electron microscope (SEM) equipped with nanometer pattern generation system (NPGS) was used to define the patterns. After development, a metal film of silver (Ag) or gold (Au) having a thickness of about 30 nm, with 2 nm chromium (Cr) film as an adhesion layer were deposited using thermal evaporation (Elite Engineering, Singapore).

FIG. 1B shows a typical SEM (JEOL 7001F) image of SRRs on PEN with w=80 nm, where the width exhibits ±7% standard deviation after statistical analysis. It is important to note that the focus and beam alignment are very critical to achieve good pattern fidelity. For rigid substrates, the fabricating procedure is the same as Metaflex process.

Example 3

Characterisation Methods

The transmission spectra of the metamaterials fabricated were taken on a microspectrophotometer (Craic 2000) in the range of 300 nm to 1700 nm. To predict the spectrum thereby providing a guide in pattern design even before fabrication and measurement, finite-difference time-domain (FDTD) calculations based on MIT Electromagnetic Equation Propagation (MEEP) codes were performed, with the dielectric constant of Ag based on Drude model obtained from Blaber et al. (Blaber et al., J. Phys. Chem. C, 2009, 113, 3041-3045).

Figure 2:
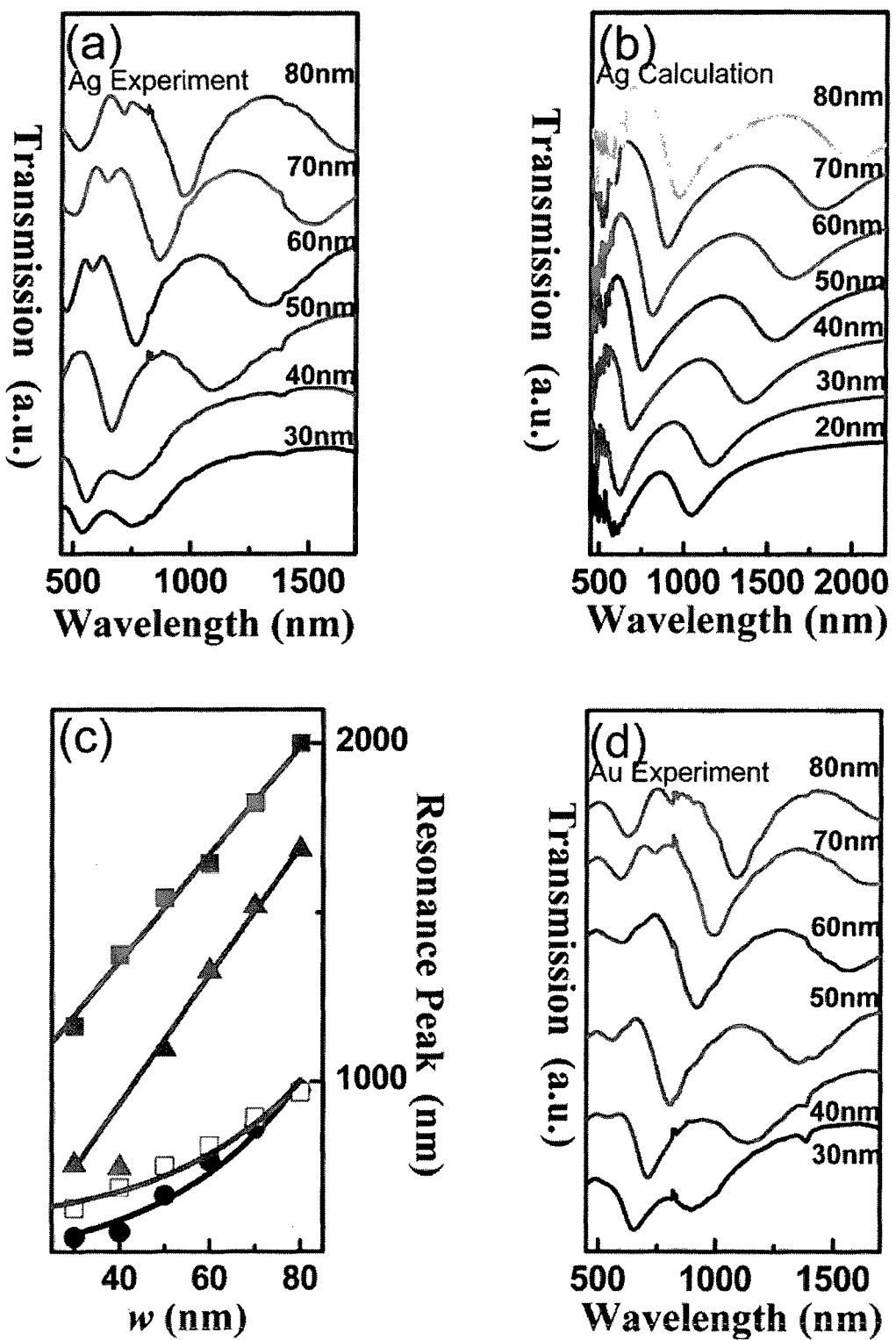
FIG. 2A is a graph showing experimental transmission spectra of SRRs with different side widths of w as shown in FIG. 1 for silver (Ag) metamaterials.
FIG. 2B is a graph showing calculated transmission spectra of SRRs by finite-difference time-domain (FDTD) for silver (Ag) metamaterials.
FIG. 2C is a graph showing experimental magnetic resonance peaks (red triangles), experimental electric resonance peaks (black circles), calculated magnetic peaks (green squares), and calculated electric resonant peaks (blue unshaded squares) as a function of w for Ag metamaterials. The curves in FIG. 2C are fitting curves as discussed later in the description.
FIG. 2D is a graph showing experimental transmission spectra of SRRs with different side widths of w for gold (Au) metamaterials.
FIG. 2E is a graph showing calculated transmission spectra of SRRs for Au metamaterials.
FIG. 2F is a graph showing experimental magnetic resonance peaks (red triangles), experimental electric resonance peaks (black circles), calculated magnetic peaks (green squares), and calculated electric resonance peaks (blue unshaded squares) as a function of w for Au metamaterials. The curves in FIG. 2F are fitting lines as discussed later in the description.
Figure 2:
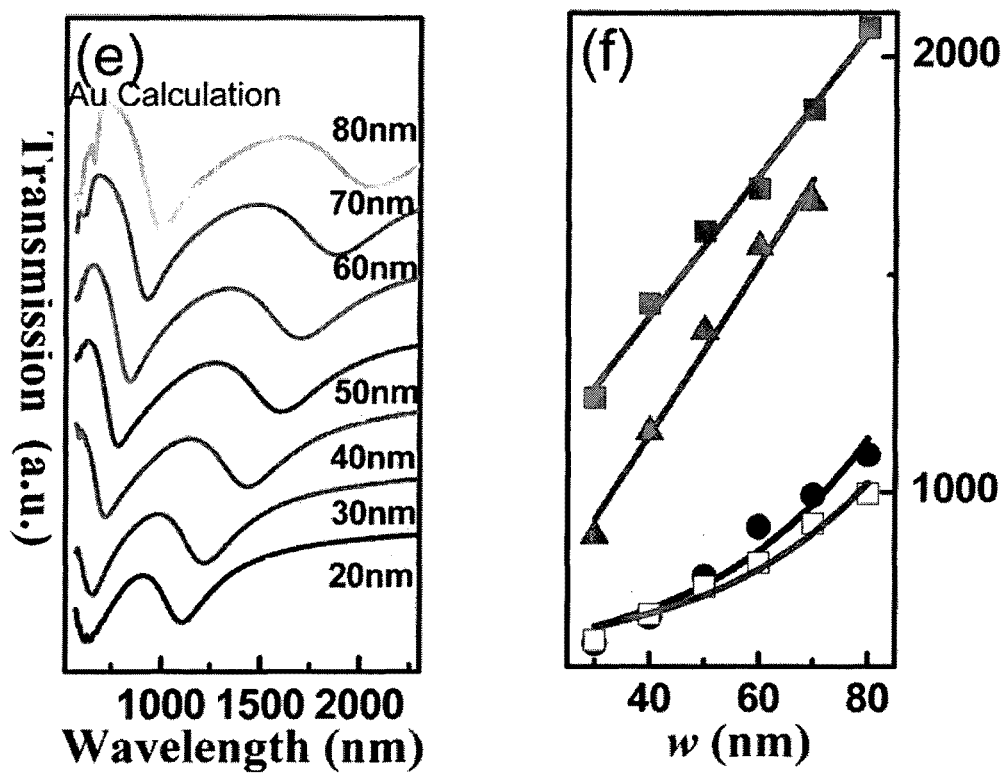

FIG. 2A displays transmission spectra of metamaterials comprising Ag-based SRRs of various w values. Two main absorption peaks were identified. The absorption peak in the shorter wavelength corresponds to the electric resonance and has been tuned to the visible region of the electromagnetic spectrum. With an increase of size i.e. increase in value of w, the electric response exhibits a systematic red-shift.

The other absorption peak in the longer wavelength of the transmission spectra corresponds to the magnetic response, and has been tuned from the mid-infrared (1687 nm) to the visible region (756 nm). As in the case for the electric resonance, the magnetic response also shows red-shifts as the size of SRRs increases. The magnetic response is due to the molecular loop current when electric polarization takes place along the gap-bearing side of the SRRs. As an unpolarized light source was used in the experiments, the calculations carried out were performed by averaging the polarization effect for both transverse magnetic (TM) and transverse electric (TE).

The inventors of the present invention have found that the fundamental magnetic response at 756 nm (396.6 THz) of metamaterials according to various embodiments of the invention represents the highest frequency so far in visible region with SRRs-based metamaterials. The weak peaks on the shorter wavelength side before the electric resonance absorption peaks in FIG. 2A and FIG. 2B may be the result of high order multipolar modes.

Example 4

Computer Simulation

Computer simulation was also carried out using different w values for the metamaterials that have been fabricated. The simulation results are depicted in FIG. 2B, which is a graph showing calculated transmission spectra of SRRs by FDTD for Ag metamaterials, and suggest a good agreement with the experimental spectra obtained. The slight difference may be attributed to the size distribution of the patterns resulting from fabrication.

FIG. 2D is a graph showing experimental transmission spectra of SRRs with different side widths of w for Au metamaterials. FIG. 2E is a graph showing calculated transmission spectra of SRRs for Au metamaterials. FIG. 2D and FIG. 2E show the results of the experimental and calculated transmission spectra for metamaterials comprising Au-based SRRs of various w values. The electric response resonances shifted from 1088 to 653 nm, while the magnetic response resonances shift from a value greater than 1700 nm (which is out of our measurement region) to 902 nm. The peak positions of the experimental spectra and simulations are extracted and plotted in FIG. 2C and FIG. 2F as a function of wavelength for various w values for Ag and Au respectively.

Referring to FIG. 2C, it is a graph showing experimental magnetic resonance peaks (red triangles), experimental electric resonance peaks (black circles), calculated magnetic peaks (green squares), and calculated electric resonant peaks (blue unshaded squares) as a function of w for Ag metamaterials. The curves in FIG. 2C are fitting curves.

Example 4.1

Electric Resonance

In FIG. 2C, the circle points are the experimental values of electric resonance and the solid curve is the fitting line with an empirical formula of $$\lambda = \lambda_0 + a \cdot \exp(w/w_1) \quad \text{Equation (1)}$$

where $\lambda$ denotes the resonance wavelength position (nm); w denotes the value of w for SRR used (nm); $w_1$ denotes the least width of the SRR patterns (30 nm in the experiments carried out); $\lambda_0$ denotes the convergence of the fitting, and a denotes the growth ratio demonstrating the scaling behavior.

This empirical formula captures the main physics embodied in our observations. From the results obtained, $\lambda_0 = (446 \pm 27)$ and $a = 39 \pm 4$. $\lambda_0$ approaches the resonant wavelength of localized plasmon resonance (LPR) of silver nanoparticles in the range of 400 nm-600 nm, and is the limit of electric response when the size of the SRR is further decreased. The calculated size dependence of the resonance position shows a similar dependence with the experiments with the squared points (blue). Using the same formula for fitting, we obtained $\lambda_0 = (562 \pm 21)$ nm and $a = 31 \pm 3$.

Two factors may affect the scaling behavior of the SRRs metamaterials according to the invention. The first factor is the resonance wavelength which is red-shifted with increase in size of the unit cells of SRRs. From the LC (inductor-capacitor) resonance point of view, the resonance frequency can be expressed as a combination of capacitance and inductance with the formula $$\omega_{LC} = (LC)^{-1/2} \quad \text{Equation (2)}$$

where $\omega$ denotes the radian frequency; L denotes the inductance (henrys) and C denotes the capacitance (farads). Accordingly, by applying the equation, as capacitance and inductance increase with an increase in unit cell size, the resonance frequency decreases.

The second factor is the coupling between unit cells due to the decrease in periodicity. For the metallic particle-particle interaction, the coupling between the unit cells results in an exponential decay of resonances, and blue shifts with increasing particle-particle distance. From the results obtained, such as that shown in FIG. 2A, the red shift in absorption peak as unit size and periodicity increase suggests that the main factor affecting the scaling behavior of the SRRs metamaterials is the first factor.

It has been demonstrated herein that an electric resonance near 542 nm for Ag with SRR-based metamaterials can be achieved by directly patterning on plastic substrates by electron beam lithography (EBL) fabrication. To our best knowledge, this is the first time such a short wavelength in the visible region can be achieved for SRR-based metamaterials.

FIG. 2F is a graph showing experimental magnetic resonance peaks (red triangles), experimental electric resonance peaks (black circles), calculated magnetic peaks (green squares), and calculated electric resonance peaks (blue unshaded squares) as a function of w for Au metamaterials. The curves in FIG. 2F are fitting lines. The experimental data of electric resonance peaks in FIG. 2F show the similar dependence on the unit size for Au metamaterials as for Ag metamaterials. The fitting for experimental data for Au metamaterials yields $\lambda_0=591\pm36$ nm and $a=37\pm4$.

Example 4.2

Magnetic Response Resonance

The resonance peak of the magnetic response for Ag metamaterials shows a linear dependence on size with an intercept of approximately $177\pm34$ nm and a slope of $19\pm1$ nm as shown in FIG. 2C. The experimental point falls outside the fitting line for magnetic resonance at 40 nm probably due to deviation of size, especially the arms of SRRs, which will influence the formation of the loop current. The coupling between the artificial magnetic dipoles is weaker compared with the electric dipoles, which shows exponential dependence on resonance wavelength.

From dipole-dipole interaction point of view, the quasi-static interaction energy $\Delta E$ is written as $$\Delta E = \gamma \frac{p_1 p_2}{4\pi\varepsilon_0 r^3} \qquad \text{Equation (3)}$$

where r is the distance between dipoles $p_1$ and $p_2$, $\gamma$ is the interaction index, which is 1 for transverse coupling (in our case for the magnetic resonance) and 2 for longitudinal coupling (in our lateral coupling for electrical resonance). Considering the electrical dipoles are stronger than the magnetic dipoles (with sharper electric resonance compared with magnetic resonance), the coupling of electric dipoles is stronger than that of magnetic dipoles. FIG. 2C also displays the unit size dependence of the calculated resonance position with an intercept of $717\pm26$ nm and a slope of $16\pm1$ nm. The combination of red shift in wavelength due to unit size increase and coupling between SRRs results in the linear dependence of the magnetic resonance peak on unit cell size. Similar results have been shown for Au metamaterials as in FIG. 2F with the linear fitting.

Example 5

Substrate

Polyethylene naphthalate (PEN) was chosen as the plastic substrate because it has a high glass transition temperature ($T_g \approx 125°$ C.) than some other polymers such as poly(ethylene terephthalate) (PET $T_g \approx 80°$ C.). PEN is also solvent, acid, and base resistant. Flexible PEN substrate has a Young's modulus (E) of 280 MPa (characteristics of physical properties by Teijin DuPont Films Co.) and the PEN substrates used have thickness (t) of about 125 μm. The transparency in the visible and near-infrared region is over 80%, which is adequate for transparent photonic devices. In addition, the mechanical characteristics of PEN make it ideal to test how optical properties of metamaterials respond to the strain of the out-of-plane direction.

Figure 3:
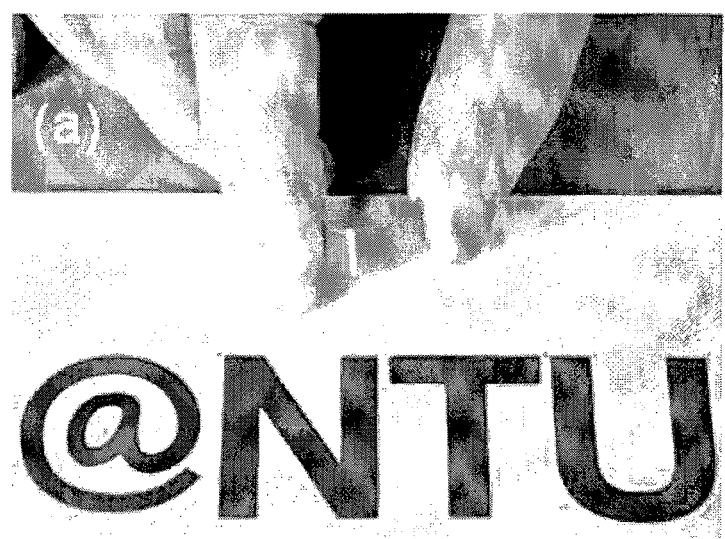
FIG. 3A is a picture of a metamaterial fabricated on a flexible substrate (termed herein as "Metaflex") taken with a background of Nanyang Technological University (NTU) campus magazine to demonstrate the flexibility.
FIG. 3B is graph showing transmission spectra of Metaflex (i) before, and (ii) after applying the strain, showing high tunability with an out-of-plane strain.
Figure 3:
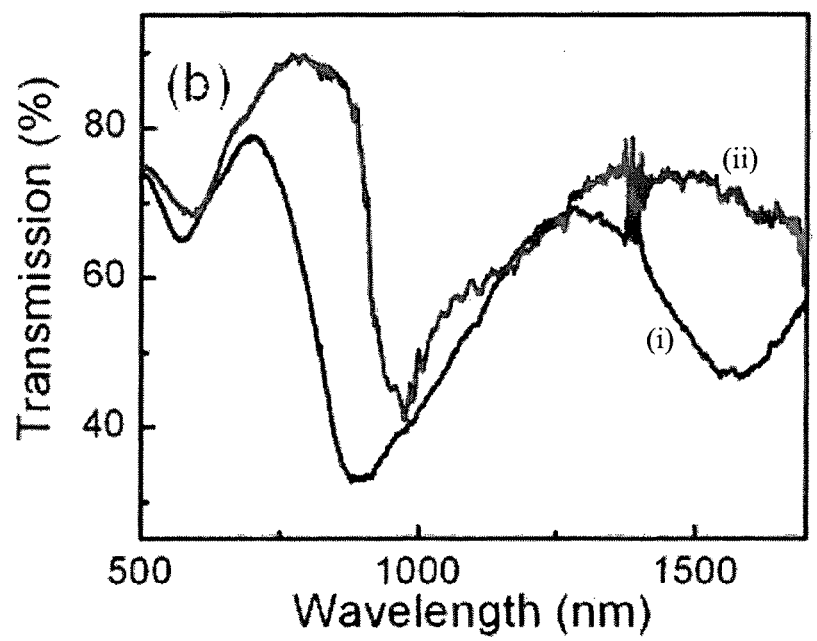

FIG. 3A demonstrates the strain sensing by PEN-based metamaterials of Au with w=50 nm with a deflection ratio of 1%. From the stress $\delta=t/\rho=4.4\times10^{-6}$ ($\rho$ is the radius of the arc after bending), the strain $\sigma=E\delta$ is approximately 1232 Pa.

FIG. 3B is graph showing transmission spectra of Metaflex (i) before, and (ii) after applying the strain, showing high tunability with an out-of-plane strain. The electric peak position shifts from 894 nm (before) to 973 nm (after), giving a net shift of 79 nm, while the magnetic response has moved out of our measurable region. The strain sensitivity was estimated to be about 0.06 nm/Pa.

Accordingly, it has been demonstrated herein a direct EBL fabrication of metamaterials on plastic substrate PEN, which can also be used to integrate into a photonic device compatible with modern optical techniques such as a remote strain sensor to monitor vibrations for some precision instruments.

Example 6

Effect of Change in Local Dielectric Environment on Performance of Metamaterials in Optical Frequency Regime There are two classes of plasmon based sensing methods reported in the literature. One is based on the surface Plasmon polariton (SPP), which has been successfully applied to biochemistry and medical research. Another type is based on the localized plasmon resonance (LPR) from the colloidal nanoparticles. It has been shown that the refractive index sensitivity does not exceed 100-300 nm per refractive index unit (RIU) in visible spectral interrogation. Recently, Kabashin et al. (Nat. Mater. 2009, 867-871) utilized the combination of LPR and SPP in a plasmonic nanorod array and demonstrated an enhanced sensitivity to the refractive-index variations of the medium between nanorods. Gu et al. (J. Appl. Phys. 2011, 109, 023104-6) also proved that an X-shape nanohole can increase the sensitivity due to the electric field enhancement created by LPR. Plasmonic nanoholes or nanorods have been used as an excellent sensing platform for a variety of applications such as live viruses and glucose solution.

According to the effective medium theory, the resonance frequency of metamaterials is very sensitive to the surrounding refractive index. For instance, dielectric overcoating or multilayer dielectric sandwiching methods have been used to tune the absorption resonance position of metamaterials in the terahertz regime.

To investigate how metamaterials in optical frequency regime respond to the change of local dielectric environment, we spin-coated a layer of PMMA onto the metamaterials surface with a thickness of approximately 200 nm. The refractive index of PMMA in the visible and infrared regions is 1.488. PMMA on metamaterials acts as a good model to evaluate how the resonances of metamaterials vary as the dielectric environment changes, providing a direct measurement of the figure of merit of the sensitivity. We also used another photoresist (Shipley 1805) with a refractive index of about 1.68 in the visible and infrared regions.

Figure 4:
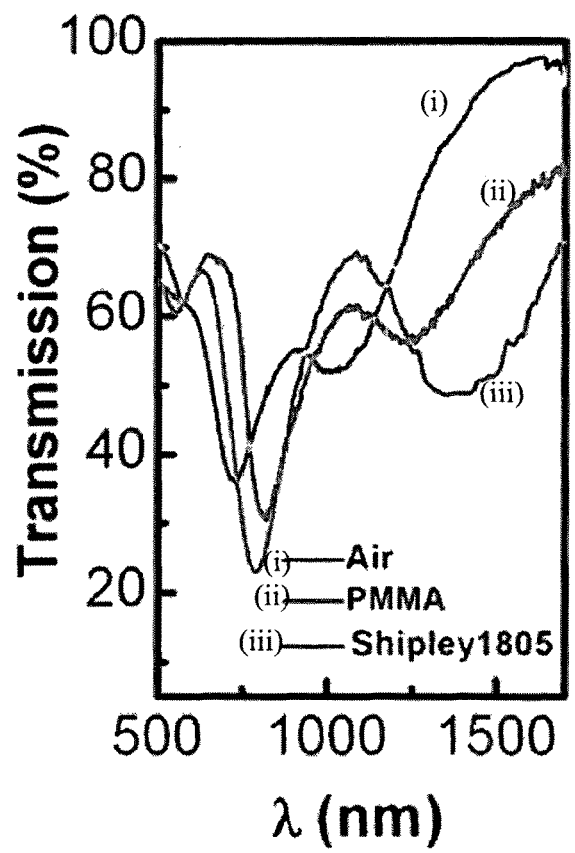
FIG. 4A is a graph showing transmission spectra of Metaflex (Au film with w=40 nm) taken in (i) air, (ii) with a layer of poly(methyl methacrylate) (PMMA), and (iii) with a layer of Shipley 1805.
FIG. 4B is a graph showing (i) electric, and (ii) magnetic resonance peak positions as a function of refractive index.
FIG. 4C is a graph showing calculated SRRs transmission with (i) PMMA and (ii) without PMMA by FDTD. The values indicated in both graphs reflect the changes of the electric and magnetic modes with a layer of PMMA.
Figure 4:
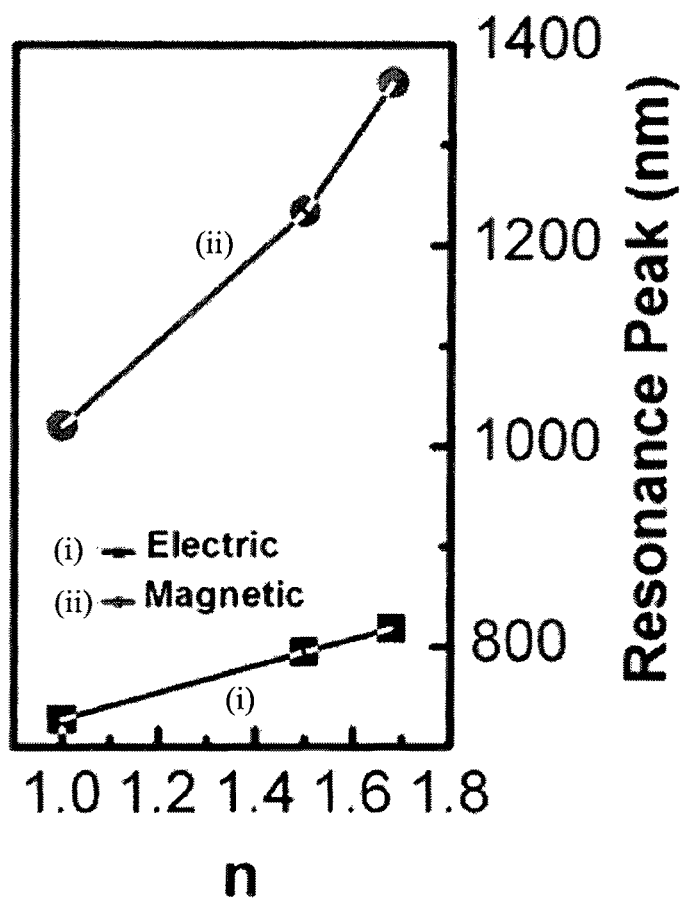
Figure 4:
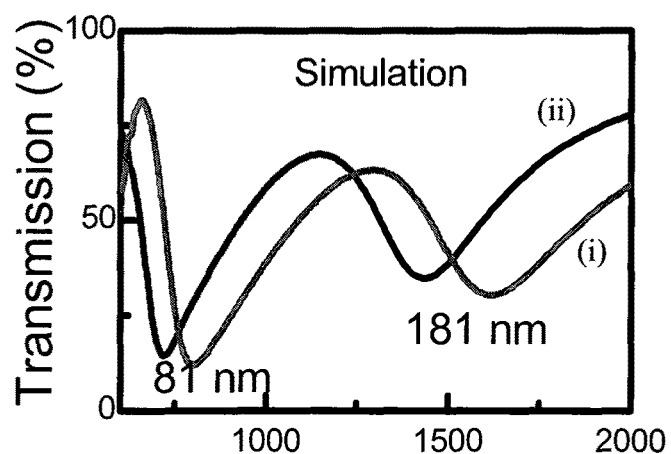

FIG. 4A displays the experimental transmission spectra taken in (i) air (black line), (ii) with a thin layer of PMMA (red line), and (iii) a thin layer of Shipley 1805 (blue line) for the Metaflex with a w=40 nm. Since Au is more inert than Ag with well established surface functionality, we will focus on Au-based metamaterials for the following sensing applications. The shift for the electric resonance is approximately 67 nm upon PMMA coating and that of the magnetic resonance is approximately 213 nm. The Shipley 1805 also shows similar results with a 90 nm shift in electric mode resonance and a 341 nm shift in magnetic resonance mode. The sensitivity is estimated to be 137 nm/RIU and 436 nm/RIU for the electric and magnetic responses respectively.

The resonance peak position change with local environmental refractive index change is shown in FIG. 4B, which is a graph showing (i) electric; and (ii) magnetic resonance peak positions as a function of refractive index. The sensitivity of the electric response is comparable to that of the gold nanoparticles based localized surface plasmon biosensing, while the sensitivity evaluated based on magnetic resonance increases by more than twice compared with the electric response.

As a bi-anisotropic component, SRRs show not only the electric response due to the collective oscillations of free electrons in metallic nanostructures, but also the artificial magnetic response due to the electrical field induced molecular loop current at normal incidence. The constitutive relationship between electric component (E), magnetic component (H), electric displacement (D), and magnetic field (B) may respectively be represented by the following equations, $$D = \epsilon_0 \epsilon_r E + \xi H/c \quad \text{Equation (4)}$$

$$B = \mu_0 \mu_r H + \chi E/c \quad \text{Equation (5)}$$

where $\epsilon_r$ is the relative permittivity and $\mu_r$ is the relative permeability, while $\chi$ and $\xi$ are the coupling coefficients of magnetic and electric fields in the SRRs respectively.

For electric response, the sensing mechanism stems purely from the response of $\epsilon_r$ change from the microenvironments. This mechanism has been applied for both SPP and LPR and also for the electric resonance in SRRs.

On the other hand, the magnetic response in SRRs originates from the $\chi$, which is due to the coupling of the electrical field and magnetic field. $\chi$ can be modeled by a magnetic coil with an inductance L (metal ring) coupled with a capacitance C (the slit of the ring) and the resonance frequency $\omega_{LC} = (LC)^{-1/2}$.

It has been suggested that the capacitance consisted of two contributions: one is the gap capacitance ($C_g$) of the SRRs, while the other is fringing-field capacitance ($C_f$), which depends on the permittivity $C_f \propto \epsilon_0 \int \epsilon(v) E(v) dv$ and the thickness of the thin film that exists between SRRs and the PEN substrate. The electric resonance is primarily determined by $C_f$, which is highly dependent on the dielectric environment, while the magnetic resonance is related not only to the $C_f$ but also to the $C_g$. Therefore, magnetic resonance exhibits higher sensitivity to the surrounding environment.

Example 7

Evaluation of Metamaterial in Sensing
(Non-Specific Interaction)

The high sensitivity of the Metaflex resonance in response to a local effective refractive index change as discussed in Example 6 suggests potential applications in chemical and biological sensing. An important category of biomolecules in biosensing is protein, which includes a variety of biomarkers that are extremely important for disease diagnosis and analysis.

To evaluate whether and how our Metaflex in optical frequency regime detect protein molecules, we used a well-known model protein of bovine serum albumin (BSA) with a molecular weight of 66776 Da. The BSA powder was first dissolved in distilled water with a concentration of 15 µM, and then the solution was diluted to change the concentration from the original 15 µM to 15 nM. The BSA solution was drop-casted on the Metaflex surface, which was then dried under room temperature. Hence, the protein molecules were non-specifically bound to the metamaterials surface. Transmission spectra were taken afterward under the microspectrophotometer. After the measurement, the same chip was soaked in the distilled water, and carefully cleaned with a heavy rinse of distilled water plus an oxygen ($O_2$) plasma treatment at 50 W for 30 s. This cleaning method was proven to be effective by re-taking the transmission spectra, which gave identical spectra obtained from the same sample before applying BSA. Then a different concentration sample was prepared and measured.

Figure 5:
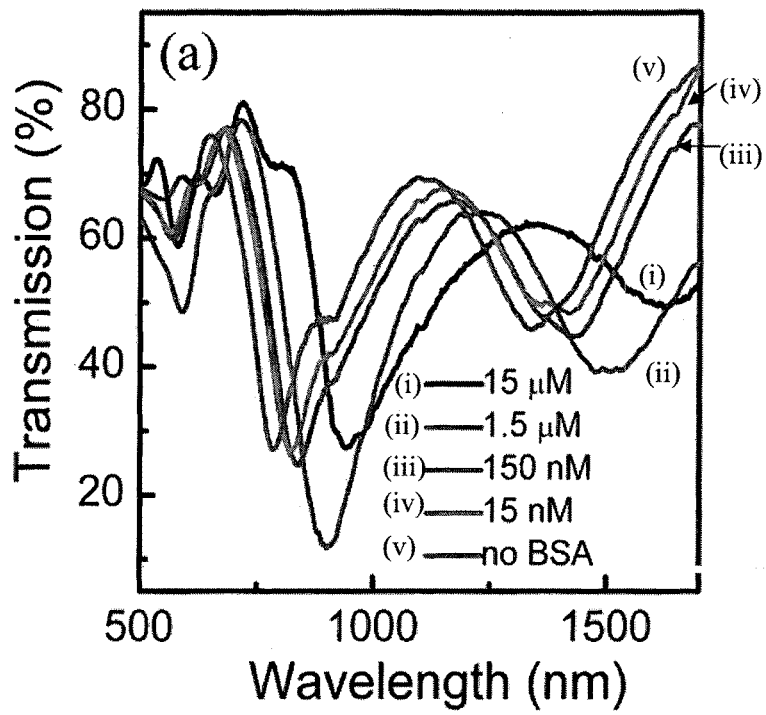
FIG. 5A is a graph showing transmission spectra of the same Metaflex sample after different bovine serum albumin (BSA) concentration treatment for (i) 15 µM (ii) 1.5 µM (iii) 150 nM, (iv) 15 nM, and (v) no BSA (provided as reference).
FIG. 5B is a graph showing (i) electric, and (ii) magnetic resonance peak shift as a function of concentration with SRRs. The solid curves are empirical fittings as discussed later in the description.
Figure 5:
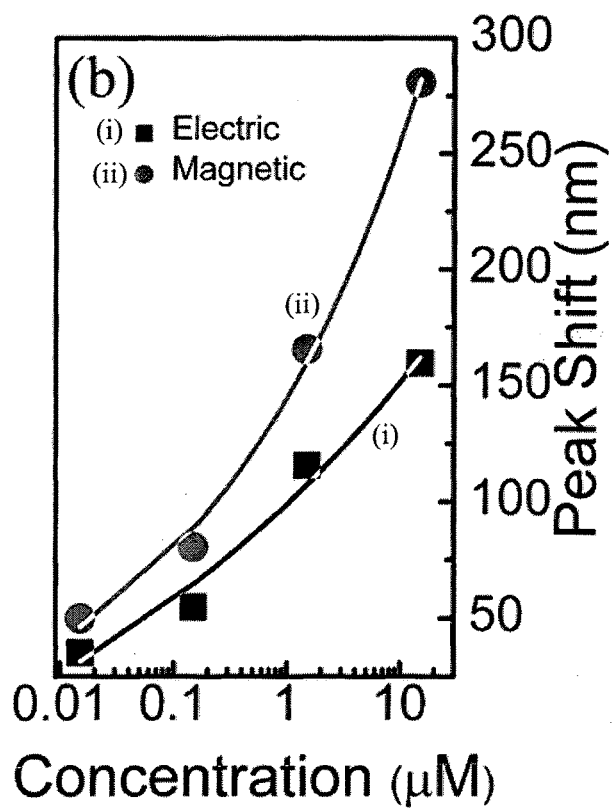

FIG. 5A is a graph showing transmission spectra of the same Metaflex sample after different BSA concentration treatment for (i) 15 µM (ii) 1.5 µM (iii) 150 nM, (iv) 15 nM, and (v) no BSA (provided as reference). As can be seen from the figure, both the magnetic and electric response modes are significantly red-shifted.

The concentration dependence of the peak position is extracted and plotted in FIG. 5B, which is a graph showing (i) electric, and (ii) magnetic resonance peak shift as a function of concentration with SRRs, with red dots representing magnetic resonance and black squares for electric resonance. The solid curves are the least-squares fitting with a formula $$\lambda_{shift} = a + b \times [M]^c \quad \text{Equation (6)}$$

where [M] is the concentration. The sensitivity can be approximately written as $$d\lambda_{shift}/d[M] = bc \times [M]^{c-1} \quad \text{Equation (7)}$$

For a concentration of 15 nM, this can reach 1.8 nm/nM for electric response and 4.5 nm/nM for magnetic response. It is important to note that the sensitivity can be further increased by metamaterial design. For example, a trapped resonance mode was recently demonstrated to exhibit a high quality factor when the structural symmetry was broken, thus higher sensitivity resulted.

Example 8

Evaluation of Metamaterial in Sensing (Specific Interaction)

The interaction between BSA and Au metamaterials surface is still non-specific. Specific chemical interaction is needed to further extend the applications of metamaterials to chemical and biological sensing. The metamaterial Au surface can be functionalized via covalent thiol chemistry, and therefore labelling can be readily achieved using thiol-terminated functional groups, e.g., thiolated biotin.

Here we further demonstrate a chemical sensing of a monolayer of thiol-terminated molecules that are covalently bound to Au metamaterials surface. Metamaterials based surface chemical sensing offers a very promising field for sensing applications, which provides a complementary detection besides well-accepted surface-enhanced Raman scattering (SERS) and SPP. The high tunability in the whole range of vis-IR spectra regime offers unique advantages to tune the interaction between analyte molecules and surface plasmon, which is not possible in thin film SPP biosensing.

As a preliminary demonstration, 2-naphthalenethiol (Sigma-Aldrich, USA) was chosen as a model molecule as schematically shown in FIG. 6A, which is a schematic diagram of chemical sensing of 2-naphthalenethiol using Metaflex. For simplicity, only one 2-naphthalenethiol molecule was drawn on each SRR.

To prepare the sample, 2-naphalenethiol powder was dissolved in ethanol with a concentration of 10 mM. The PEN-based Au metamaterial was soaked in the solution for 24 hours and then was heavily rinsed with ethanol followed by drying with nitrogen gas. To evaluate whether the molecule is indeed chemically bound to metamaterials, Raman scattering spectroscopy was conducted on the Metaflex surface using a micro-Raman spectrometer (Horiba-JY T64,000) excited with a solid state laser ($\lambda$=785 nm) in the backscattering configuration. The backscattered signal was collected through a 50× objective and dispersed by a 1800 g/mm grating, and the laser power on the sample surface was measured to be about 2.5 mW.

FIG. 6B shows the Raman spectra of 2-naphthalenethiol on metamaterial with two polarization configurations (i) perpendicular or (ii) parallel as shown in FIG. 6A, (iii) from 2-naphthalenethiol powder, (iv) from clean PEN substrate without metamaterials, and (v) from Au film on the same chip from top to bottom, respectively.

The Raman peak around 1379.4 $cm^{-1}$ due to ring-ring stretching was chosen as a comparison. The control spectrum from 2-naphthalenethiol powder shows a ring-ring stretching mode at about 1381.5 $cm^{-1}$, which suggests about 2 $cm^{-1}$ red shift on the metamaterial surface, probably due to charge transfer between gold and the 2-naphthalenethiol molecule. Usually, chemical absorption by the thiol molecules will modify the Raman polarizability tensor, and hence shift the vibrational mode frequency and change Raman intensity as well.

The Raman band about 1390.9 $cm^{-1}$ from PEN as shown in the control spectrum is due to naphthalene ring vibrational mode in PEN. It is important to note that no Raman signal from 2-naphthalenethiol was detected from a Au thin film on the same chip; hence both the thickness and reaction conditions are the same as Metaflex, while the Raman signal from 2-naphalenethiol molecules linked to Metaflex is exceptionally strong. This enhancement is a typical electromagnetic enhancement in the SERS effect.

After that, the transmission spectra of metamaterial structures after 2-naphthalenethiol functionalization were obtained. FIG. 6C is a graph showing transmission spectra of SRRs (i) without 2-naphthalenethiol, and (ii) with 2-naphthalenethiol, the inset is the zoom-in view of the spectra around the magnetic resonance mode. Both peak shifts due to molecule binding are labeled.

Figure 6:
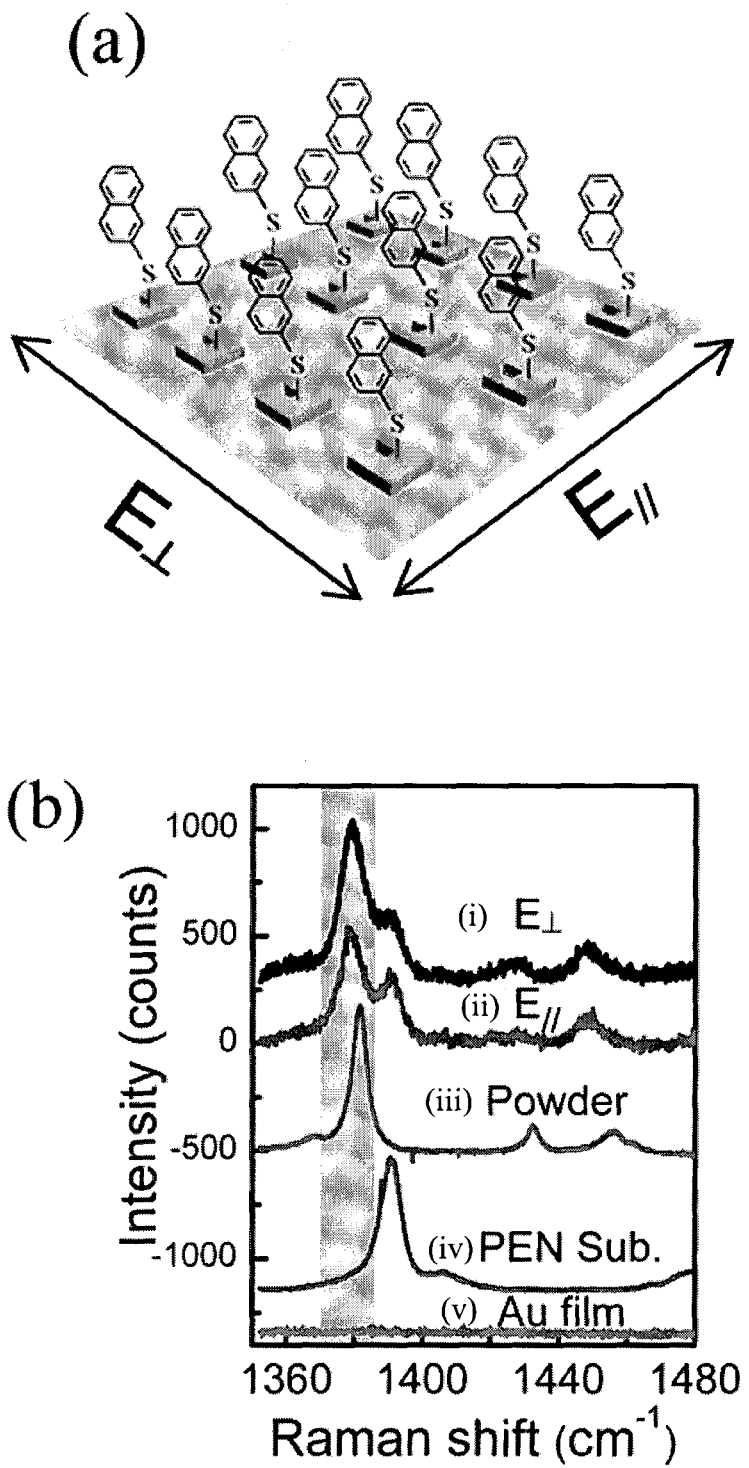
FIG. 6A is a schematic diagram of chemical sensing of 2-naphthalenethiol using Metaflex. For simplicity, only one 2-naphthalenethiol molecule was drawn on each SRR.
FIG. 6B is a graph showing Raman spectra of 2-naphthalenethiol on a Metaflex sample with polarization (i) perpendicular or (ii) parallel as shown in FIG. 6A; (iii) from 2-naphthalenethiol powder; (iv) from a clean polyethylene napthalate (PEN) substrate; and (v) from a gold film on the same PEN substrate (from top to bottom, spectra were shifted upwards in the graph for clarity), respectively.
FIG. 6C is a graph showing transmission spectra of SRRs (i) without 2-naphthalenethiol, and (ii) with 2-naphthalenethiol, the inset is the zoom-in view of the spectra around the magnetic resonance mode. Both peak shifts due to molecule binding are labeled.
Figure 6:
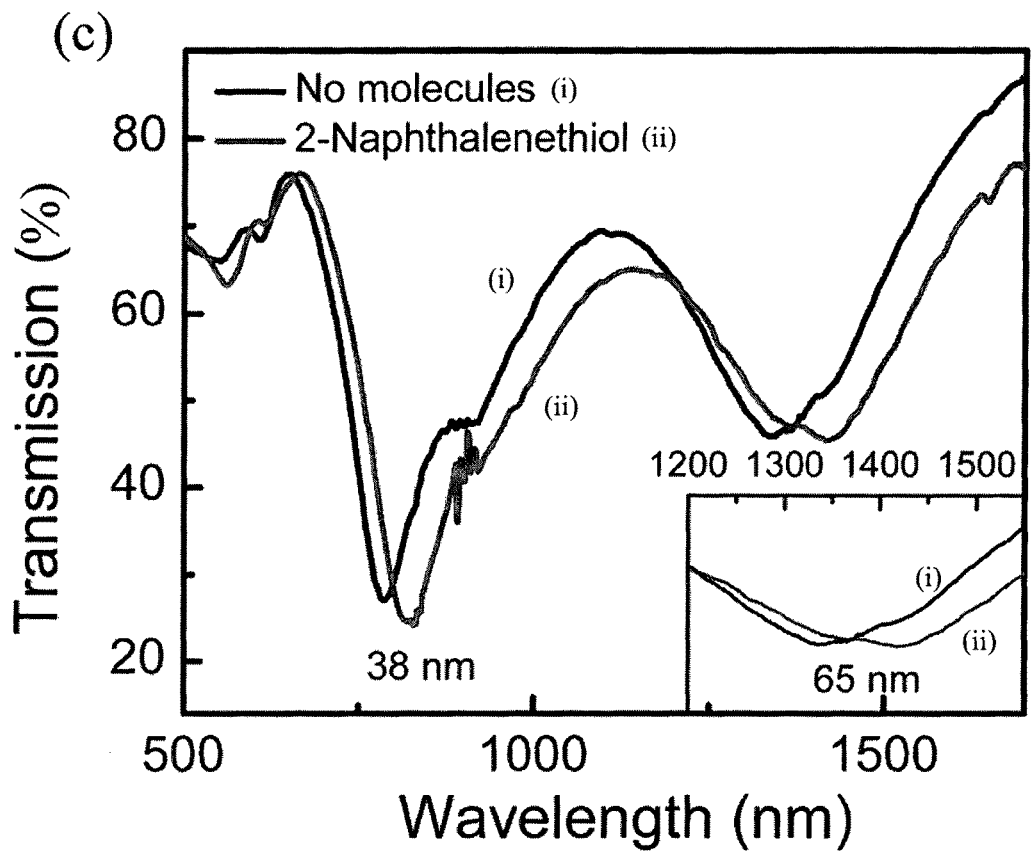

Compared with spectra taken from bare metamaterials on PEN, the absorption resonance peak exhibits a red shift of about 38 nm for electric resonance mode and about 65 nm for magnetic mode as shown clearly in FIG. 6C and inset, respectively. Unlike the data shown in FIGS. 4 and 5, which are due to the local change of dielectric constant due to binding/coating of PMMA or BSA, the significant peak shift in FIG. 6 stems from only the surface chemical modification due to a single layer of 2-naphthalenethiol, which is merely on the order of 1 nm thick. Such a significant change of resonance peak of metamaterials due to a single layer chemical molecule binding has not been well studied in the metamaterials community. The results obtained demonstrate the possibility of sensitive detection and correlation between the peak shift and the length of molecules that bind to the surface. Complemented with a strong SERS effect, our Metaflex photonic devices can provide multiple channel reading for chemical and/or biosensing applications.

In summary, SRR based Metaflex operating in the visible-IR optical frequency regime has been experimentally realized by EBL. We demonstrated the least line width of fabrication on plastic substrate of about 30 nm, which exhibited the lowest electric resonance near 542 nm and a magnetic response near 756 nm. Flexible metamaterials, particularly their magnetic resonance, exhibit high sensitivity response to strain, local dielectric environment, and surface chemical change in the visible-IR region, with a sensitivity as high as 436 nm/RIU, which may be attributable to the electric and magnetic field coupling in SRRs. Two model chemical/biological sensing applications have been carried out and it has been demonstrated that our metamaterials exhibited a sensitivity of about 4.5 nm/nM for non-specific BSA protein binding, and an extraordinary 65 nm peak shift due to a monolayer of 2-naphthalenethiol molecule covalent binding. With recent progress in large scale imprinting lithography, our work suggests that Metaflex operating in the visible-IR region exhibits numerous potential applications in large scale, low-cost, transparent, and portable photonic devices for strain and chemical/biological sensing.

Besides the flexible substrates, above-mentioned biosensing based on absorption band shifts and SERS also can be achieved on rigid substrates in Vis-IR region (termed herein as "Metarigid"). Although the Metarigid is strainless sensing channel, it has strength on hardness requirement devices. Metaflex and Metarigid complement each other's advantages.

Example 9

Effects of Geometry of Unit Cell of SRR on Metamaterial Response

It has been found that the optical response of metamaterials is highly sensitive to the geometry symmetric of unit cell shape. Therefore, we also fabricated different size and different symmetric geometry unit cell such as S-shape, H-shape, V-shape and Y-shape metamaterials.

As an example, we show rigid metamaterials fabricated on ITO coated glass. The details parameters are shown in FIG. 7. The periodicities of the unit cell along x-axis and y-axis are 200 nm and 350 nm for (A) S-, (B) H- and (C) Y-shape, respectively. The x-axis and y-axis are the same 200 nm for (D) V-shape.

To push the electric response from infrared to visible region, the whole unit size of SRRs including the unit cell is reduced down to 60% (100% corresponds to original size defined in FIG. 7 with w=50 nm), which decreases the w from 50 nm to 30 nm. Besides the V-shape, the other three geometries have been configured based on the U-shaped SRR prototype.

Beside the substrates (flexible or rigid), our Vis-IR metamaterials supply three optional ways to obtain the best enhancement: (1) geometry symmetric shape, (2) the unit cell size of specific shape, and (3) exciting laser energy. One or more ways may be varied to get the best SERS signal for specific molecules. This highly designable technique shows a very robust potential in bio-sensing and chemical-sensing applications.

We use the same experimental condition as described for U-shaped SRRs to measure the SERS signal of 2-naphthalenethiol molecules linked to the S-, H-, V- and Y-shape metamaterials.

For polarization measurements, the gap of U-shaped prototype was used as the reference. For example, the parallel (perpendicular) polarization means the laser polarization is parallel (perpendicular) the gap of U-shape. For Y-shape, we use the top-U as the reference. We also use the gap of V as the polarization measurement reference for V-shape.

The specific SERS enhancement factor depends the hot spots properties, such as area, numbers and enhanced intensity; exciting laser energy; and optical response of specific metamaterials. The SERS results are shown in FIGS. 8A to 8D. FIGS. 8E to 8H are the SEM images for 100% size (w=50 nm) metamaterials pattern.

From the Raman spectra depicted in FIGS. 8A to 8D, five observations may be derived: (1) the highest enhanced SERS signal strongly depends on the size and geometry of metamaterials; (2) the highest enhanced pattern has the highest polarization dependence; (3) the polarization enhancement of perpendicular to gap is much higher than one parallel to the gap of pattern unit; (4) the Y-shaped SRRs with w=30 nm gives the highest enhancement; (5) the SERS peak around 1380 $cm^{-1}$ (C—C ring stretch vibration) red shifts about 4 $cm^{-1}$ compared to bulk 2-Naphthalenethiol. We will explain it one by one as follows.

Example 9.1

Strength of SERS Signal is Dependent on Size and Geometry of Metamaterials

The size and geometry dependence of SERS intensity can be explained by resonance between photon and plasmon absorption of metamaterials. The resonance works via two routes, with the first route being incident resonance when incidence laser energy is close to the plasmon absorption peak, and the second route being the scattering resonance when scattering photon energy matches the plasmon absorption peak. The resultant SERS intensity is determined by the sum of the two resonances. In view of the above, our metamaterials allow four options to tune the SERS enhanced factor, namely (i) geometry, (ii) size, (iii) incident laser, and (iv) scattering wavelength (thus specific Raman peak).

Example 9.2

Strongest SERS Signal Shows Highest Polarization Dependence

Secondly, the strongest SERS signal shows robust polarization dependence. This phenomena can be explained that the high un-polarization ratio of Plasmon absorption at 785 nm (incident laser) or 879 nm (scattering photon at 1378 $cm^{-1}$). This high polarization dependence has a potential application in optical and magneto filter, polarization detector and sensor.

Example 9.3

Polarization Enhancement of Perpendicular to Gap is Much Higher Than One Parallel to the Gap of Pattern Unit When the laser polarization is parallel to the gap of unit pattern, the electric field of light will seal the gap of unit and it breaks the symmetry of metamaterials. Therefore, the parallel polarization should decrease the optical response of metamaterials. The converse is true for perpendicular polarization. This polarization dependence can be enhanced when the resonant happens, i.e. at the highest enhancement situation. Specially, the w=30 nm Y-shaped metamaterials have the best resonant response for 785 laser and 879 nm scattering photon, and thus the highest enhancement and un-polarization ratio.

Example 9.4

Y-Shaped SRRs with w=30 nm Provide the Highest Enhancement

For all size and geometry metamaterial substrates, about 4 $cm^{-1}$ red shift of C—C ring stretch vibration (about 1380) from 1392 $cm^{-1}$ of bulk 2-Naphthalenethiol decrease to 1378 $cm^{-1}$ of SERS signal at metamaterials. This redshift has the same charge transfer origin as explained in SERS of PEN metamaterials described previously. The charge transfer effect only depends on Fermi energy of the specific metal (such as gold or silver) and chemical potential of linked molecules. The same metal should have the same peak shift.

In conclusion, our metametrials can work in the Vis-IR region, and it can access to the shortest wavelength up to now. This Vis-IR metamaterials support many options to reach the maximum sensing, including geometry and size of unit cell, and substrates (flexible or rigid). Two sensing tunnels are claimed, one is based on absorption band shifts, and another is based on SERS effect. In SERS sensing, the polarization configuration, exciting laser energy and measured Raman band support good tunable options to get the highest enhanced signal for single molecule detection. SERS can provide chemical identification, i.e., chemical fingerprint of the analyte species, this is something that traditional plasmon biosensing cannot provide.

One type of commercial application in which the metamaterials of the invention may be used is in the area of biosensing and chemical sensing. For example, the metamaterial may be used for clinical tests and analysis. As another example, the metamaterial may be used for research study in biological and chemical laboratories. For biomedical applications, these highly sensitive photonic biosensors may be used to target a variety of biomarkers, such as prostate specific antigen (PSA) marker or bovine serum albumin (BSA), or nucleic acids such as DNA or RNA oligonucleotides.

The invention claimed is:
1. A method of fabricating a sensor having a metamaterial comprising split-ring resonators operable in the visible-infrared range, the method comprising
   a) depositing a layer of a conductive material on a non-conductive flexible substrate;
   b) forming a layer of electron beam resist on the layer of conductive material;
   c) patterning the layer of electron beam resist using electron beam lithography to form a patterned substrate;
   d) depositing a layer of a noble metal on the patterned substrate; and
   e) removing the resist to generate the metamaterial comprising the split-ring resonators having a least line width of about 20 nm to about 40 nm on the non-conductive flexible substrate.
2. A metamaterial operable in the visible-infrared range fabricated by a method, the method comprising:
   a) depositing a layer of a conductive material on a non-conductive flexible substrate;

b) forming a layer of electron beam resist on the layer of conductive material;

c) patterning the layer of electron beam resist using electron beam lithography to form a patterned substrate;

d) depositing a layer of a noble metal on the patterned substrate; and e) removing the resist to generate the metamaterial comprising split-ring resonators having a least line width of about 20 nm to about 40 nm on the non-conductive flexible substrate.

3. A sensor for chemical or biological sensing comprising a metamaterial operable in the visible-infrared range comprising split-ring resonators having a least line width of about 20 nm to about 40 nm on a non-conductive flexible substrate; and a layer of conductive material directly between the split-ring resonators and the non-conductive flexible substrate.

4. The sensor according to claim 3, further comprising linker molecules bonded to the surface of the metamaterial.

5. The sensor according to claim 4, wherein the linker molecules are covalently bonded to the surface of the metamaterial.

6. The sensor according to claim 4, wherein linker molecules comprises a functional group selected from the group consisting of thiol, amine, amide, nitro, carboxylic acid, cyano, and halogen.

7. The sensor according to claim 6, wherein the linker molecules comprise a thiol group.

8. The sensor according to claim 4, wherein the linker molecules are configured to be specifically associated with target analytes contained in a sample.

9. The sensor according to claim 8 wherein the sample is derived from biological material.

10. The sensor according to claim 8 wherein the sample comprises biomarkers.

11. The sensor according to claim 10 wherein the sample is a chemical solution.

12. The sensor according to claim 3, wherein the split-ring resonators have a least line width of about 20 nm to about 25 nm.

13. The sensor according to claim 3, wherein the split-ring resonators are C-shaped, E-shaped, H-shaped, S-shaped, U-shaped, U-bar shaped, V-shaped, W-shaped or Y-shaped.

14. The sensor according to claim 3, wherein the split-ring resonators are Y-shaped.

15. The sensor according to claim 3, wherein the split-ring resonators comprise a noble metal.

16. The sensor according to claim 15, wherein the noble metal comprises gold, silver, or alloys thereof.

17. The sensor according to claim 16, wherein the noble metal is present as a layer having a thickness of about 5 nm to about 500 nm on the surface of the split-ring resonators.

18. The sensor according to claim 17, wherein the thickness of the layer of noble metal is about 30 nm.

19. The sensor according claim 17, wherein the layer of conductive material is between the layer of noble metal and the non-conductive flexible substrate.

20. The sensor according to claim 19, wherein the layer of conductive material comprises a transparent material selected from the group consisting of indium tin oxide, indium zinc oxide, and tin oxide.

* * * * *

UNITED STATES PATENT AND TRADEMARK OFFICE
CERTIFICATE OF CORRECTION

PATENT NO. : 9,683,991 B2  
APPLICATION NO. : 14/124496  
DATED : June 20, 2017  
INVENTOR(S) : Xiong et al.

Page 1 of 1

It is certified that error appears in the above-identified patent and that said Letters Patent is hereby corrected as shown below:

In the Claims

Column 22,
Line 13, "claim 3" should read --claim 13--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*